US012734248B2

(12) United States Patent
Livney et al.

(10) Patent No.: US 12,734,248 B2
(45) **Date of Patent: *Sep. 15, 2026**

(54) COMPOSITION AND METHOD FOR A PREBIOTIC DELIVERY SYSTEM TARGETED TO PROBIOTIC BACTERIA

(71) Applicant: TECHNION RESEARCH & DEVELOPMENT FOUNDATION LIMITED, Haifa (IL)

(72) Inventors: Yoav D. Livney, Haifa (IL); Yechezkel Kashi, Haifa (IL); Stav Peled, Haifa (IL); Shay Freilich, Haifa (IL); Adi Seifert, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 939 days.

This patent is subject to a terminal disclaimer.

(21) Appl. No.: 17/841,809

(22) Filed: Jun. 16, 2022

(65) Prior Publication Data

US 2022/0305138 A1 Sep. 29, 2022

Related U.S. Application Data

(63) Continuation-in-part of application No. 16/645,892, filed as application No. PCT/IL2018/051019 on Sep. 9, 2018.

(60) Provisional application No. 62/556,437, filed on Sep. 10, 2017.

(51) Int. Cl.

| | |
|---|---|
| ***A61K 47/69*** | (2017.01) |
| ***A23L 33/21*** | (2016.01) |
| ***A61K 38/40*** | (2006.01) |
| ***A61K 47/61*** | (2017.01) |
| ***A61K 47/64*** | (2017.01) |

(52) U.S. Cl.

CPC .......... *A61K 47/6921* (2017.08); *A23L 33/21* (2016.08); *A61K 38/40* (2013.01); *A61K 47/61* (2017.08); *A61K 47/64* (2017.08)

(58) Field of Classification Search

None

See application file for complete search history.

(56) References Cited

U.S. PATENT DOCUMENTS

2014/0322340 A1 10/2014 Livney

FOREIGN PATENT DOCUMENTS

| | | |
|---|---|---|
| CN | 106820156 A | 6/2017 |
| WO | 2012091946 A1 | 7/2012 |
| WO | 2014099134 A1 | 6/2014 |

OTHER PUBLICATIONS

Manninen (Nutrition & Metabolism 2009,6:38).*

Weichert et al. ("Bioengineered 2'-fucosyllactose and 3-fucosyllactose inhibit the adhesion of Pseudomonas aeruginosa and enteric pathogens to human intestinal and respiratory cell lines" Nutrition research 33 (2013)831-838).*

Hernandez-Hernandez et al. (Proteomics, 2010, 10, 3699-3711).*

Castanys-Munoz (2'fucosyllactose: an abundant, genetically determined soluble glycan present in human milk Nutrition reviews vol. 71, issue 12 pp. 773-789).*

Raikos, Vassilios, and Theodore Dassios. "Health-promoting properties of bioactive peptides derived from milk proteins in infant food: a review." Dairy science & technology 94 (2014): 91-101. doi: 10.1007/s13594-013-0152-3. Epub Oct. 16, 2013. PMID: 24511365; PMCID: PMC3912356.

Manninen, Anssi H. "Protein hydrolysates in sports nutrition." Nutrition & metabolism 6, No. 1 (2009): 1-5. doi: 10.1186/1743-7075-6-38. PMID: 19785737; PMCID: PMC2761917.

Böger, M., Van Leeuwen, S.S., Lammerts van Bueren, A. and Dijkhuizen, L., 2019. Structural identity of galactooligosaccharide molecules selectively utilized by single cultures of probiotic bacterial strains. Journal of Agricultural and Food Chemistry, 67(50), pp. 13969-13977.

Muthaiyan, A., Hernandez-Hernandez, O., Moreno, F.J., Sanz, M.L. and Ricke, S.C., 2012. Hydrolyzed caseinomacropeptide conjugated galactooligosaccharides support the growth and enhance the bile tolerance in Lactobacillus strains. Journal of agricultural and food chemistry, 60(27), pp. 6839-6845.

W. H. Holzapfel et al., "Overview of gut flora and probiotics", Int J Food Microbiol, vol. 41 Issue 2 pp. 85-101, 1998.

Harry J. Flint et al., "The role of the gut microbiota in nutrition and health", Nat Rev Gastroenterol Hepatol, vol. 9 Issue 10 pp. 577-589, 2012.

R. A. Rastall, "Bacteria in the gut: friends and foes and how to alter the balance", J Nutr, vol. 134 Suppl 8 pp. 2022S-2026S, 2004.

Taylor C. Wallace et al., "Human gut microbiota and its relationship to health and disease", Nutr Rev, vol. 69 Issue 7 pp. 392-403, 2011.

Glenn R. Gibson et al., "Dietary modulation of the human colonic microbiota: updating the concept of prebiotics", Nutr Res Rev, vol. 17 Issue 2 pp. 259-275, 2004.

Guidelines for the Evaluation of Probiotics in Food. Report of a Joint FAO/WHO Working Group on Drafting Guidelines for the Evaluation of Probiotics in Food. London Ontario, Canada. 2002.

María José Martin et al., "Microencapsulation of bacteria: A review of different technologies and their impact on the probiotic effects", Innov Food Sci Emerg Technol, vol. 27 pp. 15-25, 2015.

(Continued)

*Primary Examiner* — Tara L Martinez

(74) *Attorney, Agent, or Firm* — The Roy Gross Law Firm, LLC; Roy D. Gross

(57) ABSTRACT

Provided herein is a particle made of a protein or a peptide covalently bound to a prebiotic carbohydrate, thereby forming a conjugate. The particle may be used for selectively promoting probiotic bacteria growth in the intestine, particularly the colon and may be used to selectively deliver additional probiotic growth factors, or other bioactives and drugs to probiotic bacteria in the intestine, particularly to the colon. Furthermore, provided herein are methods for preparing the particle, and for delivering a substance bound to, or entrapped within the particle, into the gastrointestinal tract of a subject in need thereof.

9 Claims, 11 Drawing Sheets

(56) References Cited

OTHER PUBLICATIONS

P. Marteau and B. Flourié, "Tolerance to low-digestible carbohydrates: symptomatology and methods", Br J Nutr, vol. 85 Suppl 1 pp. S17-S21, 2001.
Arthur C. Ouwehand et al. "Prebiotics and other microbial substrates for gut functionality", Curr Opin Biotechnol vol. 16 Issue 2 pp. 212-217, 2005.
Cornelia Liepke et al., "Human milk provides peptides highly stimulating the growth of bifidobacteria", Eur J Biochem vol. 269 Issue 2 pp. 712-718, 2002.
Karina Pokusaeva et al., "Carbohydrate metabolism in Bifidobacteria". Genes Nutr, vol. 6 Issue 3 pp. 285-306, 2011.
Daniel Garrido et al., "Utilization of galactooligosaccharides by *Bifidobacterium longum* subsp. *infantis* isolates", Food Microbiol, vol. 33 Issue 2 pp. 262-270, 2013.
Ganzle MG. Galacto-Oligosaccharides, in Fuquay, JW (ed.), Encyclopedia of Dairy Sciences 2nd ed. Elsevier Ltd. vol. 3, p. 209-216. 2011.
Antonio Alberto Zuppa et al, "Prebiotics and Probiotics in Infant Nutrition", in Book Probiotics, Prebiotics, and Synbiotics, pp. 101-134, 2016.
Paolo Manzoni, "Clinical Benefits of Lactoferrin for Infants and Children", J Pediatr, vol. 173 Suppl S43-S52, 2016.
P-W. Chen et al, "Antimicrobial potential for the combination of bovine lactoferrin or its hydrolysate with lactoferrin-resistant probiotics against foodborne pathogens", J Dairy Sci, vol. 96 Issue 3 pp. 1438-1446, 2013.
Kearney N, Stanton C, Desmond C, Coakley M, Collins JK, Fitzgerald G, Ross RP. Culturing of bifidobacteria, in Farnworth, ER (ed.), Handbook of Fermented Functional Foods, 2nd ed. CRC Press, pp. 37-39, 2008.
Mans Minekus et al., "A standardised static in vitro digestion method suitable for food—an international consensus", Food and Function, vol. 5 Issue 6 pp. 1113-1124, 2014.
Tatsuya Masuko et al., "Carbohydrate analysis by a phenol-sulfuric acid method in microplate format", Anal Biochem, vol. 339 Issue 1 pp. 69-72, 2005.
Oliver H. Lowry et al., "Protein measurement with the Folin phenol reagent", J Biol Chem, vol. 193 Issue 1 pp. 265-275, 1951.
María Luz Sanz et al: "Characterization and in Vitro Digestibility of Bovine [beta]-Lactoglobulin Glycated with Galactooligosaccharides", J. Agric. Food Chem. 2007, 55, 7916-7925.
Alice M. Moscovici et al: "The impact of the Maillard reaction on the in vitro proteolytic breakdown of bovine lactoferrin in adults and infants", Food Funct., 2014, 5, 1898.
Fabíola Cristina de Oliveira et al: "Food Protein-Polysaccharide Conjugates obtained via the Maillard Reaction: A Review", Critical reviews in food science and nutrition, vol. 56, No. 7, May 13, 2014, pp. 1108-1125.
Buchert et al. "Crosslinking Food Protiens for Improved Functionality" Annu. Rev. Food Sci Techonol. 2010, 1:113-38.
Li, Y., Zhong, F., Ji, W., Yokoyama, W., Shoemaker, C.F., Zhu, S. and Xia, W., 2013. Functional properties of Maillard reaction products of rice protein hydrolysates with mono-, oligo-and polysaccharides. Food Hydrocolloids, 30(1), pp. 53-60.
Peled, S. and Livney, Y.D., 2021. Oligosaccharide-lactoferrin shell-crosslinked particles for selective targeting of proteins to probiotic bacteria in the colon. Food Hydrocolloids, 120, p. 106973.
Patel, S., Goyal, A. The current trends and future perspectives of prebiotics research: a review. 3 Biotech 2, 115-125 (2012). https://doi.org/10.1007/s13205-012-0044-x.
PCT International Search Report for International Application No. PCT/IL2018/051019, mailed Dec. 11, 2018, 6pp.
PCT Written Opinion for International Application No. PCT/IL2018/051019, mailed Dec. 11, 2018, 5pp.
Mukhopadhya, A. and Sweeney, T., 2016. Milk proteins: Processing of bioactive fractions and effects on gut health. In Milk Proteins—From Structure to Biological Properties and Health Aspects. IntechOpen. DOI:10.5772/63509.

* cited by examiner

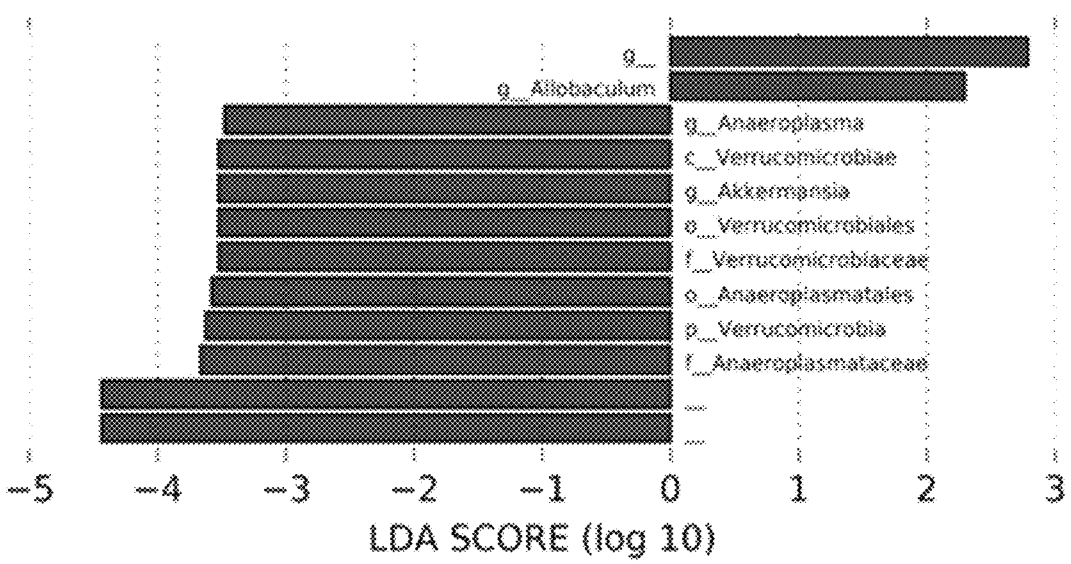
FIGURE 6D
Control
Blank
a: __
b: __
c: g__Allobaculum
d: g__
e: g__Anaeroplasma
f: f__Anaeroplasmataceae
g: o__Anaeroplasmatales
h: g__Akkermansia
i: f__Verrucomicrobiaceae
j: o__Verrucomicrobiales
FIGURE 6E

COMPOSITION AND METHOD FOR A PREBIOTIC DELIVERY SYSTEM TARGETED TO PROBIOTIC BACTERIA

CROSS-REFERENCE TO RELATED APPLICATIONS

This application is a continuation-in-part of U.S. patent application Ser. No. 16/645,892, titled "COMPOSITION AND METHOD FOR A PREBIOTIC DELIVERY SYSTEM TARGETED TO PROBIOTIC BACTERIA", filed Mar. 10, 2020, which is a national phase of PCT Patent Application No. PCT/IL2018/051019, filed Sep. 9, 2018, which claims the benefit of priority of U.S. Provisional Patent Application No. 62/556,437 filed Sep. 10, 2017 the contents of which are incorporated herein by reference in their entirety.

FIELD OF THE INVENTION

The present invention is in the field of prebiotics.

BACKGROUND OF THE INVENTION

The human gut microbiota has long been known for its importance to gut health. The majority of the human gut microbiome is colonizing the distal gut, with about $10^{12}$ microbial cells per gram of wet feces, with great diversity of species in the adult gut. Human health is greatly affected by the human gut microbiota, which is involved with various substantial functions: supplying the host with nutrients, supporting digestion of complex foods, preventing invasion of pathogens by competition, by maintaining a barrier and by promoting immune homeostasis. One of the most influential factors on both human health and performance of the gut microbiota is the diet. Depending on our dietary intake, the gut microbiota can produce either advantageous compounds that provide protection against host disease, or adverse compounds associated with human disease. In a healthy gastrointestinal tract, which is partially colonized by probiotic bacteria (naturally symbiotic bacteria which confer benefits to the host) such as bifidobacteria and lactobacilli, the probiotics can inhibit pathogen overgrowth and entry to host cells. These microorganisms are believed to exert biological effects through a phenomenon known as colonization resistance, whereby the indigenous anaerobic flora limits the concentration of potentially pathogenic (mostly aerobic) flora in the digestive tract. Other modes of action, such as supplying enzymes or influencing enzyme activity in the gastrointestinal tract, may also account for some of the other physiologic effects that have been attributed to probiotics. Gastrointestinal health strongly depends on the fermentation products of the probiotic bacteria, such as short chain fatty acids which generally promote colonic health and protection from pathogens. A disrupted homeostasis of the gut microbiota has been found to increase the risk for obesity, to increase toxin and carcinogen production, to cause intestinal putrefaction, bowel diseases, liver infections and more.

Prebiotics are indigestible food ingredients that beneficially affect host health by selectively stimulating the growth and/or activity of one or a limited number of probiotic bacteria in the intestine, particularly the colon. Prebiotics are selectively fermentable ingredients that allow specific changes, both in the composition and/or activity of the gastrointestinal microflora that confer benefits upon host wellbeing and health. For example, fructo-oligosaccharides (FOS), galacto-oligosaccharides (GOS) and lactulose.

Probiotics and prebiotics play an important role in human nutrition. The main effects attributed to selected probiotics/prebiotic products have been proved by clinical trials, while others have been acquired on the basis of in vitro tests which require in vivo transposition in order to be validated.

The main clinical reports in the literature for the application of probiotics have been done for the treatment of infectious diseases including viral, bacterial or antibiotic associated diarrhea, relief of chronic bowel inflammatory diseases, immuno-modulation, lowering of serum cholesterol, decreased risk of colon cancer, improve lactose digestion, reduce allergies, and effect on intestinal microbiota. Although the extensive investigation of the health benefits, information on probiotic species, a specific strain-therapeutic application, and sufficient dosages, is not sufficiently studied to allow practical and rational consumption. The limitation of ingesting probiotics, whether in functional foods or in dietary supplements, is their low survival during the manufacturing process (high temperature and shear), storage (moisture, temperature, oxygen), and transit through the gastrointestinal tract (low pH in the stomach and bile salts in the small intestine). Some of these issues are dealt with by microencapsulation of the probiotics, though this raises their cost and the extra processing steps may further lower viability during manufacture. Furthermore, encapsulated probiotics' particle size is considered too large for many food applications, as their grainy texture is perceptible. In addition, most of the studies indicate that modulation of the gut microbiota by oral probiotic administration only lasts for few days and therefore requires long-term daily intake to maintain. As for prebiotics, dose-related intolerance symptoms may appear after their ingestion (bloating, abdominal cramps, diarrhea), although, a daily dose of prebiotics <20 g/day is generally well tolerated. Moreover, none of the existing solutions for modulation of the gut microbiota contains a protein source. Proteins and their amino acids are an important nitrogen source for bacteria, but are relatively scarce in the gut (most amino acids are present at concentrations below 0.01 mM in the human colonic content), as most protein digestion products are absorbed in the small intestine. The digestion products of some proteins have been shown to selectively stimulate growth of probiotic gut bacteria.

SUMMARY OF THE INVENTION

According to some embodiments of the present invention, there is provided a particle comprising a plurality of conjugates, wherein each conjugate comprises a protein covalently bound to a prebiotic carbohydrate, wherein at least two of the conjugates are covalently linked via the prebiotic carbohydrate.

According to one aspect, there is provided a particle comprising a plurality of conjugates, wherein: each conjugate comprises a peptide covalently bound to a prebiotic carbohydrate; the peptide is a hydrolysate of a protein obtained via hydrolysis of the protein by a protease selected from the group consisting of: a gastric protease, an intestinal protease, including any functional analog thereof, or any combination thereof; and the prebiotic carbohydrate comprises a mammalian milk oligosaccharide.

According to another aspect, there is provided a composition comprising a plurality of particles as disclosed herein, wherein the composition is in a form of (i) a powder, or (ii)

in a form of a suspension further comprising a nutraceutical or a pharmaceutically acceptable carrier.

According to another aspect, there is provided a method of increasing the abundance, activity, or both, of a probiotic bacteria in the colon of a subject, comprising the step of administering to the subject a nutritionally or a therapeutically effective amount of a composition as disclosed herein, thereby enriching probiotic bacteria in the colon of a subject.

According to another aspect, there is provided a method of delivering an agent to the gastrointestinal tract of a subject, comprising the step of administering to the subject a nutritionally or a therapeutically effective amount of the composition disclosed herein, thereby delivering an agent to the gastrointestinal tract.

According to another aspect, there is provided process for producing a particle, wherein the process comprises: (a) contacting a protein with a protease in an aqueous solution under conditions suitable for hydrolyzation of the protein, thereby obtaining a plurality of peptides; (b) covalently bonding the plurality of peptides and a prebiotic carbohydrate under conditions suitable for performing a Maillard reaction, thereby forming a plurality of Maillard conjugates; and (c) subjecting the plurality of Maillard conjugates to the conditions suitable for self-assembly of the Maillard conjugates, thereby forming the particle; wherein: the protease is selected from the group consisting of a gastric protease or an intestinal protease, including any functional derivative, or any combination thereof; the prebiotic carbohydrate is or comprises a mammalian milk oligosaccharide.

In some embodiments, the mammalian milk oligosaccharide comprises 2'-Fucosyllactose including any stereoisomer, and any derivative thereof.

In some embodiments, the protease comprises at least two distinct protease species.

In some embodiments, the prebiotic carbohydrate is at least 60% indigestible by non-ruminant mammals and wherein the prebiotic carbohydrate is an intestinal prebiotic-fermentation substrate.

In some embodiments, the conjugates are at least partially cross-linked within the particle.

In some embodiments, the protein is a food acceptable protein selected from the group consisting of: an animal protein, a plant protein, an algal protein, a microbial protein, and any combination thereof.

In some embodiments, the protein is selected from the group consisting of: a milk protein, a lactoferrin, a transferrin, and a casein, and any combination thereof.

In some embodiments, (i) the average size of the particle is in the range of 10 nm to 3,000 nm; (ii) the weight ratio of the peptide to the prebiotic carbohydrate in the particle is in the range of 1:10 to 10:1, respectively; or (iii) any combination of (i) and (ii).

In some embodiments, the particle comprises a core and a shell, wherein the core comprises at least 70% by weight of the peptide and the shell comprises at least 70% by weight of the prebiotic carbohydrate.

In some embodiments, the core, the shell, or both further comprises a prebiotic nutritional agent, a therapeutic agent, a prebiotic growth factor, or any combination thereof.

In some embodiments, the conjugate is Maillard conjugate.

In some embodiments, the probiotic bacteria belong to the genus *Akkermansia*.

In some embodiments, the probiotic bacteria is *Akkermansia muciniphila*.

In some embodiments, increasing activity comprises (i) increasing production, secretion, or both, of short chain fatty acids (SCFAs); (ii) reducing production, secretion, or both, of ammonia, or (iii) any combination of (i) and (ii), by the probiotic bacteria.

In some embodiments, the delivering is to a location selected from a distal gut or a colon of the subject; optionally wherein the agent is selected from the group consisting of: a therapeutic agent, a prebiotic nutritional agent, and a prebiotic growth factor.

In some embodiments, the protease comprises at least two protease two distinct protease species, optionally selected from pepsin, rennin, trypsin, and chymotrypsin, including any functional derivatives, or any combination thereof; and optionally the process further comprises a step of crosslinking the Maillard conjugates under suitable conditions, optionally wherein crosslinking is performed via a crosslinking agent.

In some embodiments, the prebiotic carbohydrate is at least 60% indigestible by a mammal. In some embodiments, the prebiotic carbohydrate is an intestinal prebiotic-fermentation substrate.

In some embodiments, the prebiotic carbohydrate is selected from the group consisting of dietary fibers, galacto-oligosaccharide, fructo-oligosaccharide, inulin, resistant starch, raffinose, lactulose, stachyose, verbascose, transgalactosylated oligosaccharides, isomalto-oligosaccharides, pyrodextrins, soy-oligosaccharides, pectic-oligosaccharides, xylo-oligosaccharides, levans, synthetic or isolated mammalian milk oligosaccharides, and any combination thereof.

In some embodiments, the covalent bond is via a primary amine of the protein to a carbonyl of the carbohydrate. In some embodiments, at least two conjugates are covalently linked via a phospho-di-ester bond between a carbohydrate of a first conjugate and a carbohydrate of a second conjugate.

In some embodiments, the protein is selected from, without being limited thereto, a whole protein, and a protein hydrolysate, and any combination thereof. In some embodiments, the protein is selected from, without being limited thereto, an animal protein, a plant protein, an algal protein and a microbial protein, and any combination thereof. In some embodiments, the protein selected from, without being limited thereto, a milk protein, a lactoferrin, a transferrin, and a casein, and any combination thereof.

In some embodiments, the protein is a hydrolysate by a protease selected from, without being limited thereto, a gastric protease or an intestinal protease, or any combination thereof.

In some embodiments, the average size of a diameter of the particle is in the range of 10 nm to 3000 nm.

In some embodiments, the weight ratio of the protein to the carbohydrate in the particle is in the range of 1:10 to 10:1, respectively.

In some embodiments, the particle comprises a core and shell, wherein the core comprises at least 80% by weight of the protein and the shell comprises at least 80% by weight of the carbohydrate. In some embodiments, the core, the shell or both further comprises a prebiotic nutritional agent. In some embodiments, the core, the shell or both further comprises a therapeutic agent. In some embodiments, the core, the shell or both further comprises a prebiotic growth factor.

According to some embodiments of the present invention, there is provided a composition comprising a plurality of particles, as described herein, wherein the plurality of particles is in a form of a suspension. In some embodiments, the composition is in the form of an agglomerate of particles. In some embodiments, the composition in the form of a powder. In some embodiments, the composition is an oral composition.

According to some embodiments of the present invention, there is provided a method of enriching probiotic bacteria in the intestine of a subject, comprising the step of administering to the subject a nutritionally or a therapeutically effective amount of the composition described herein.

According to some embodiments of the present invention, there is provided a method of delivering an agent to the gastrointestinal tract of a subject, comprising the step of administering to the subject a nutritionally or a therapeutically effective amount of the composition described herein. In some embodiments, the delivering is to a location selected from the intestine, the distal gut or the colon of the subject. In some embodiments, the agent is a therapeutic agent. In some embodiments, the agent is a prebiotic nutritional agent. In some embodiments, the agent is a prebiotic growth factor.

According to some embodiments of the present invention, there is provided a process for producing the particle described herein, the process comprises: (a) covalently bonding a protein and a prebiotic carbohydrate, thereby forming a conjugate; and (b) crosslinking at least two conjugates via the carbohydrate. In some embodiments, the covalently bonding comprises contacting the protein and the carbohydrate in an aqueous solution, and incubating the solution for 0.5-5 h at 40-100° C. In some embodiments, the covalently bonding comprises contacting the protein and the carbohydrate in an aqueous solution, drying the solution, thereby forming a powder; and incubating the powder at 50-70° C. at 75-85% relative humidity for 1-72 h. In some embodiments, the crosslinking comprises providing the conjugate, adding a crosslinking compound at a pH solution of at least 8, and incubating the solution for 1-12 h at 20-50° C. In some embodiments, the crosslinking compound is selected from, without being limited thereto, sodium trimetaphosphate (STMP), monosodium phosphate (SOP), sodium tripolyphosphate (STPP), and phosphoryl chloride (POCL3), or any combination thereof.

In some embodiments, the process comprises a step of hydrolyzing the protein prior to forming the conjugate, comprising: (i) contacting the protein with a protease in an aqueous solution, and (ii) incubating the solution for 0.5-5 h at 25-45° C. In some embodiments, the protein is a hydrolysate of a protease selected from a gastric protease or an intestinal protease, or any combination thereof.

In some embodiments, the process further comprises a step of entrapping an agent selected from, without being limited thereto, a prebiotic growth factor, a nutraceutical, a prebiotic nutritional agent, or a therapeutic agent, or any combination thereof, comprising: contacting the compound with the conjugate prior to step (b) described herein.

In some embodiments, the weight ratio of the protein to the carbohydrate in the solution of step (a) described herein is in the range of 1:10 to 10:1, respectively.

Further embodiments and the full scope of applicability of the present invention will become apparent from the detailed description given hereinafter. However, it should be understood, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 6A-6F include graphs, diagrams, and a box plot. (6A) Weighted UniFrac PCoA of the gut-microbiome 16S rDNA profiling following a three-weeks feeding-program (as disclosed herein) with supplemented with: either 2'-FL-LFH (green), Unconjugated 2'-FL,LFH (control, red), or saline (blank, blue). (6B) Distribution diagram of the LDA-score of 2'-FL-LFH compared to the blank-group. (6C) Circular-cladogram of statistically-significant differences in colonic microbial clades between 2'-FL-LFH and blank-groups. (6D) Distribution diagram of the LDA-score of unconjugated 2'-FL,LFH control compared to the blank-group. (6E) Circular-cladogram of statistically-significant differences in colonic microbial clades between unconjugated 2'-FL,LFH control and blank-groups. (6F) Relative abundance of *A. muciniphila* in the different groups.

DETAILED DESCRIPTION OF THE INVENTION

The Particle

Figure 1:
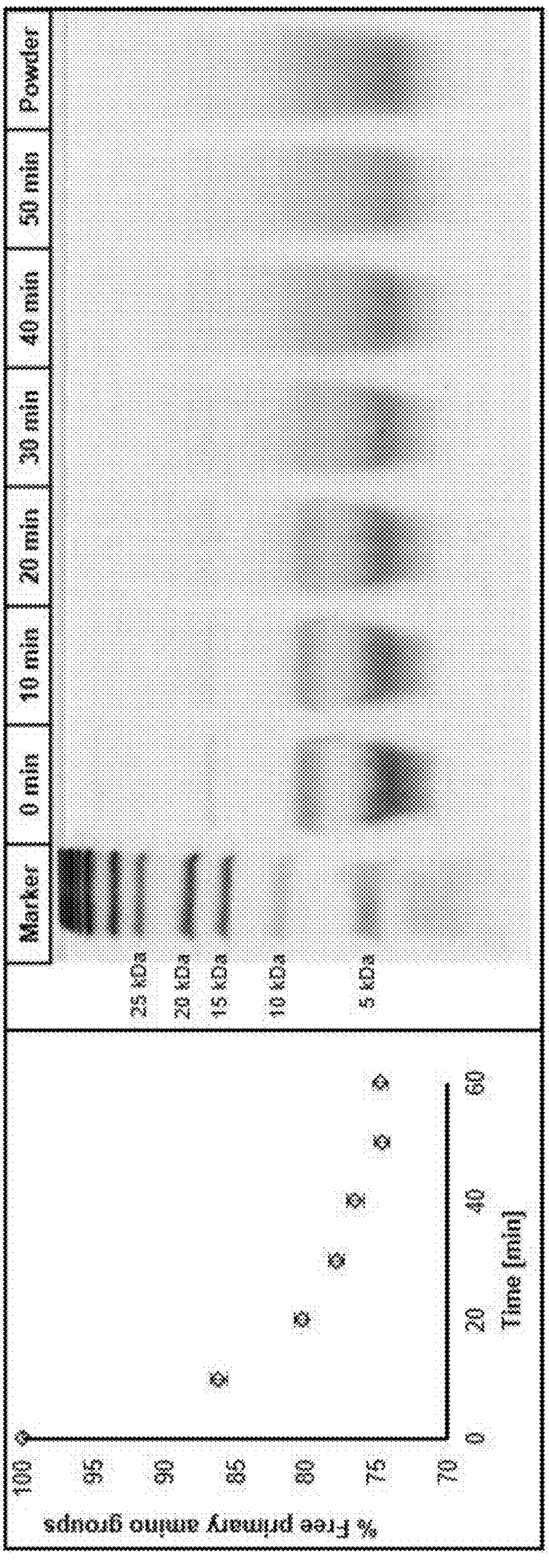
FIG. 1 depicts progression of the Maillard conjugation between galactooligosaccharides (GOS) and lactoferrin hydrolysate (LFH). Left: Percent of free primary amino groups in the LFH with Maillard reaction time, determined by the OPA assay. Right: Molecular weight distribution of the LFH-GOS particles with Maillard reaction time (0-50 min). Left lane: molecular weight size marker. Right lane: reconstituted lyophilized powder of isolated LFH-GOS conjugates.

In one aspect of the present invention, there is provided a particle comprising a plurality of conjugates, wherein each conjugate comprises a peptide covalently bound to a prebiotic carbohydrate; the peptide is a hydrolysate of a protein obtained via hydrolysis of the protein by a protease selected from the group consisting of: a gastric protease, an intestinal protease, including any functional analog thereof, or any combination thereof, simultaneously or sequentially; and the prebiotic carbohydrate comprises a mammalian milk oligosaccharide.

In some embodiments, the mammalian milk oligosaccharide is or comprises 2'-Fucosyllactose (2'-FL), including any derivative thereof, and/or any stereoisomer thereof. In some embodiments, at least one monomer of the 2'-FL stereoisomer is an enantiomer of the naturally occurring 2'-FL. In some embodiments, the prebiotic carbohydrate and/or a derivative thereof, and/or any stereoisomer thereof comprises or is derived from a mammalian milk oligosaccharide. In some embodiments, the prebiotic carbohydrate and/or a derivative thereof, and/or any stereoisomer thereof comprises or is derived from 2'-FL.

In some embodiments, each conjugate comprises a peptide derivative covalently bound to the prebiotic carbohydrate derivative. In some embodiments, covalently bound is via a covalent bond formed between carboxy, thio, or amino group of the peptide and a carbonyl, or hydroxy group of the oligosaccharide (e.g. mammalian milk oligosaccharide). In some embodiments, covalently bound is via a linker comprising a first functional moiety capable of reacting with the peptide (e.g. with carboxy, thio, or amino group of the peptide), and a second functional moiety capable of reacting with the oligosaccharide (e.g. with carbonyl, or hydroxy group of the oligosaccharide).

In some embodiments, the conjugate is or comprises a Maillard conjugate. In some embodiments, the conjugate (e.g. the Maillard conjugate) is or comprises a peptide derivative covalently bound to the prebiotic carbohydrate derivative via a Maillard reaction. A skilled artisan will appreciate, that a Maillard conjugate is formed via a reaction between a primary amine of the peptide and the carbonyl (an aldehyde or a ketone group) of the prebiotic carbohydrate, also known as the "Maillard reaction". Accordingly, the terms "peptide derivative" and "prebiotic carbohydrate derivative" including any grammatical form thereof as used herein, encompass any chemical modification of the peptide and of the prebiotic carbohydrate resulting from the conjugation thereof via a Maillard reaction.

A skilled artisan will further appreciate, that the exact structure of the prebiotic carbohydrate derivative and of the peptide derivative may vary, however various Maillard conjugates are well-known in the art. For example, the Maillard reaction includes inter alia a Schiff-base formation accompanied by Amadori rearrangement, thus the prebiotic carbohydrate derivative may encompass a dehydroxylated oligosaccharide (e.g., at 1' position); and the peptide derivative may encompass a deprotonated peptide (e.g., bound to the prebiotic carbohydrate derivative via a secondary amine).

The phrase "prebiotic carbohydrate" refers to a carbohydrate, specifically a host-indigestible carbohydrate, that beneficially affects the host by selectively stimulating the growth and/or activity of one or a limited number of bacterial species in the host's intestine, which provide benefits to the host. In some embodiments, the term "host" as used herein encompasses a non-ruminant mammal, or more specifically a human.

The phrase "indigestible carbohydrate" refers to a carbohydrate which is partially digested in the gastrointestinal tract by the action of acids (e.g., gastric acid) or digestive enzymes present in the human upper digestive tract (stomach and small intestine). In some embodiments, the prebiotic carbohydrate is an intestinal prebiotic-fermentation substrate. In some embodiments, the carbohydrate and/or the peptide of the particle of the invention are fermented by certain types of bacteria of the human intestinal microbiota (e.g., probiotic bacteria). In some embodiments, the carbohydrate and/or the peptide of the particle of the invention are fermented by the intestinal probiotic bacteria.

The phrase "probiotic bacteria" in some embodiments thereof, refers to live bacteria which when administered in adequate amounts confer benefits to the host, wherein the host is as described herein.

In some embodiments, the probiotic bacteria (e.g., intestinal probiotic bacteria) belong to the genus *Akkermansia*. In some embodiments, the probiotic bacteria are or comprise *Akkermansia muciniphila*.

In some embodiments, the constituents of the particle of the invention promotes any one of: growth, proliferation, activity (such as production of short chain fatty acids), abundance of the probiotic bacteria in the intestine of a subject (e.g., a human subject), including any combination thereof. In some embodiments, the constituents of the particle of the invention promotes any one of: growth, proliferation, activity, abundance of the probiotic bacteria in the intestine of a subject (e.g., a human subject), including any combination thereof; wherein the probiotic bacteria are or comprise bacteria belonging to the genus *Akkermansia* (e.g., *Akkermansia muciniphila*).

In some embodiments, the peptide of the invention is a hydrolysate of a food-grade protein obtained by at least partial hydrolysis of the protein by a protease selected from, without being limited thereto, a gastric protease or an intestinal protease, or any combination thereof; wherein the protein is a food-grade protein.

In some embodiments, the food-grade protein is selected from, without being limited thereto, an animal protein (e.g., derived from a mammal), a plant protein, an algal protein, and a microbial protein, and any combination thereof. In some embodiments, the protein selected from, without being limited thereto, a milk protein, a lactoferrin, a transferrin, and a casein, and any combination thereof. In some embodiments, the transferrin is selected from, without being limited thereto, lacto-transferrin (i.e., lactoferrin or LTF), Melanotransferrin (MTF), inhibitor of carbonic anhydrase (ICA) or serotransferrin (STF). In some embodiments, the casein is selected from, without being limited thereto, alpha S1 casein, alphaS2 casein, A1 beta casein, A2 beta casein, kappa casein and gamma casein.

In some embodiments, the peptide(s) of the invention comprises a hydrolysate of a protein obtained by at least partial hydrolysis of a food-grade protein by at least two distinct protease species selected from, without being limited thereto, a gastric protease or an intestinal protease, including any functional derivative or any combination thereof, hydrolyzing the protein either simultaneously, or sequentially. In some embodiments, the peptide(s) of the invention is/are obtained by contacting a food-grade protein with at least two distinct protease species, as described herein. In some embodiments, at least two distinct protease species are selected from pepsin, rennin, trypsin, and chymotrypsin, including any functional derivatives, or any combination thereof.

In some embodiments, the gastric protease or the intestinal protease encompasses a human gastric protease or intestinal protease. In some embodiments, the gastric protease or the intestinal protease encompasses an isolated enzyme. In some embodiments, the functional derivative of the gastric protease or of the intestinal protease encompasses any isolated or synthetic enzyme having a similar proteolytic activity as the native human gastric and/or intestinal protease. In some embodiments, the functional derivative encompasses any analogue characterized by a structure similarity and/or homology of at least 80%, at least 85%, at least 90%, at least 95%, at least 97%, at least 99% to the native human enzyme, including any range between.

In some embodiments, the functional derivative encompasses any acidic protease. In some embodiments, the functional derivative encompasses any isolated or synthetic enzyme characterized by substantially the same cleavage profile (e.g., by facilitating hydrolytic cleavage of the food-grade protein at substantially the same position), as the native human gastric and/or intestinal protease. In some embodiments, the functional derivative encompasses any isolated or synthetic enzyme configured to facilitate proteolysis of the food-grade protein, so as to obtain a plurality of peptides which are substantially stable upon gastric and/or intestinal digestion.

In some embodiments, the peptides and/or the particles disclosed herein remain substantially intact upon human gastric and/or intestinal digestion, or upon conditions similar thereto (e.g., under simulated digestion conditions, which are well known in the art). In some embodiments, the term "substantially intact" refers to at least 20%, at least 30%, at least 40%, at least 50%, at least 60%, at least 70%, at least 80%, at least 90% of the initial weight of the particles, peptides, and/or the Maillard conjugates, including any range between.

According to some embodiments of the present invention, there is provided a particle comprising a plurality of Maillard conjugates, wherein at least two of the Maillard conjugates are covalently cross-linked. In some embodiments, crosslinking is via a crosslinking agent. In some embodiments, crosslinking comprises a covalent bond between two units, each independently selected from a prebiotic carbohydrate unit and a peptide unit. In some embodiments, crosslinking is an intramolecular cross-link. In some embodiments, crosslinking is an intermolecular cross-linking between two Maillard conjugates. In some embodiments, crosslinking is between a first Maillard conjugate and a second Maillard conjugate, wherein (i) a prebiotic carbohydrate unit and/or a peptide unit of the first Maillard conjugate is bound to (ii) a prebiotic carbohydrate unit and/or a peptide unit of the second Maillard conjugate. In some embodiments, a prebiotic carbohydrate unit and/or a peptide unit of the first Maillard conjugate is bound to a prebiotic carbohydrate unit and/or a peptide unit of the second Maillard conjugate (i) directly (e.g., via a Maillard conjugation, via a peptide bond, etc.) or (ii) via a cross-link formed by a cross-linking agent, wherein the cross-linking agent is as described hereinbelow.

In some embodiments, the carbohydrate units of the first Maillard conjugate and of the second Maillard conjugate are covalently linked via a phospho-di-ester bond. In some embodiments, the peptide units of the first Maillard conjugate and of the second Maillard conjugate are covalently linked via an amide bond. In some embodiments, the peptide unit of the first Maillard conjugate is covalently bound to a first end of the cross-linking agent via an amide bond (e.g. an amino group of the first Maillard conjugate is bound to a carboxy group of the cross-linking agent, or vice versa). In some embodiments, the peptide unit of the second Maillard conjugate is covalently bound to a second end of the cross-linking agent via an amide bond.

The term "unit" refers herein to a single carbohydrate molecule. In some embodiments, the "unit" comprises a monomeric, oligomeric or a polymeric carbohydrate. In some embodiments, the "unit" comprises a homo-carbohydrate or a hetero-carbohydrate (i.e., comprises different monomers). In some embodiments, the covalent bond is formed between two identical "units" (i.e., a homo-cross-linking). In some embodiments, the covalent bond is formed between two different "units" (i.e., a hetero-crosslinking).

In some embodiments, the prebiotic carbohydrate is an oligosaccharide. In some embodiments, the oligosaccharide has a degree of polymerization (DP) of 2 to 100. In some embodiments, the oligosaccharide has a degree of polymerization (DP) of 2-50. In some embodiments, the oligosaccharide has a degree of polymerization between 2 and 10, between 2 and 5, between 5 and 10, including any range between.

In some embodiments, the carbohydrate is a modified or a non-modified carbohydrate, or any combination thereof. In some embodiments, the carbohydrate is a reducing sugar. In some embodiments, the carbohydrate is a polysaccharide. In some embodiments, the carbohydrate is an oligosaccharide.

The phrase "modified carbohydrate" refers herein to an enzymatically and/or a chemically driven covalent linkage of an organic group to the carbohydrate backbone, e.g., O-acetylation, O-sulfation, O-alkylation, and O-phosphorylation.

In some embodiments, the prebiotic carbohydrate is selected from the group consisting of dietary fibers, galacto-oligosaccharide, fructo-oligosaccharide, inulin, resistant starch, raffinose, lactulose, stachyose, verbascose, transgalactosylated oligosaccharides, isomalto-oligosaccharides, pyrodextrins, soy-oligosaccharides, pectic-oligosaccharides, xylo-oligosaccharides, levans, synthetic or isolated mammalian milk oligosaccharides, and any combination thereof.

In some embodiments, the covalent bond is via a primary amine of the protein to a carbonyl of the carbohydrate.

In some embodiments, the primary amine is selected from an $\varepsilon$-amino group of a lysine sidechain, or an $\alpha$-amino group of a protein N-terminus. In some embodiments, the carbonyl is of an aldehyde group of a reducing sugar.

In some embodiments, the covalent bond between the protein and the carbohydrate is a Schiff base bond. In some embodiments, the covalently bound protein and carbohydrate complex is termed as a "Maillard conjugate".

In some embodiments, the average size of the particle is in the range of 10 nm to 4000 nm. In some embodiments, the average size of the particle is in the range of 100 nm to 3000 nm. In some embodiments, the average size of the particle is in the range of 200 nm to 1500 nm.

In some embodiments, the weight ratio of the protein to the carbohydrate in the particle is in the range of 1:10 to 10:1, respectively. In some embodiments, the weight ratio of the protein to the carbohydrate in the particle is in the range of 1:1 to 10:1, respectively. In some embodiments, the weight ratio of the protein to the carbohydrate in the particle is in the range of 1:1 to 7:1, respectively. In some embodiments, the weight ratio of the protein to the carbohydrate in the particle is in the range of 2:1 to 6:1, respectively. In some embodiments, the weight ratio of the protein to the carbohydrate in the particle is in the range of 1:1 to 5:1, respectively. In some embodiments, the weight ratio of the protein to the carbohydrate in the particle is in the range of 2:1 to 5:1, respectively. In some embodiments, the weight ratio of the protein to the carbohydrate in the particle is in the range of about 3:1, respectively.

In some embodiments, the particle is a micellar particle. In some embodiments, the particle comprises a core and shell. In some embodiments, the core comprises at least 70% by weight of the protein and the shell comprises at least 70% by weight of the carbohydrate. In some embodiments, the core comprises at least 80% by weight of the protein and the shell comprises at least 80% by weight of the carbohydrate. In some embodiments, the core comprises at least 90% by weight of the protein and the shell comprises at least 90% by weight of the carbohydrate.

In some embodiments, the core, the shell or both further comprises a prebiotic nutritional agent. In some embodiments, the core, the shell or both further comprises a therapeutic agent. In some embodiments, the core, the shell or both further comprises a prebiotic growth factor.

As used herein, the term "protein" is used to refer to a polymer or an oligomer of amino acid residues. The term "protein" as used herein encompass peptides, peptidomimetics (typically including non-peptide bonds or other synthetic modifications) and the peptide analogs peptoids and semi-peptoids or any combination thereof. In another embodiment, the term "protein" apply to amino acid polymers in which one or more amino acid residue is an artificial chemical analog of a corresponding naturally occurring amino acid. In one embodiment, the particle comprises a first native protein, or fragments thereof, being bound to the carbohydrate and a second therapeutic agent being a native protein or a modified protein. In some embodiments, the term "protein" encompasses any food-grade protein, as disclosed herein, and wherein the food-grade protein comprises a whole protein a protein hydrolysate, a partially hydrolyzed protein, a processed protein, including any combination thereof.

As used herein, the term "analog" includes any peptide/protein having an amino acid sequence substantially identical to one of the sequences of the proteins specifically described herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

As used herein, the phrase "conservative substitution" also includes the use of a chemically derivatized residue in place of a non-derivatized residue provided that such peptide displays the requisite function as specified herein.

In another embodiment, the term "variant" refers to a polypeptide which comprises a modification of one or more amino acids as compared to another polypeptide. In some embodiments, the modification comprises a substitution, a deletion, and/or an insertion of one or more amino acids as compared to another polypeptide. In some embodiments, the changes may be of minor nature, such as conservative amino acid substitutions resulting in conservative amino acid substitutions that do not significantly affect the activity of the polypeptide. In some embodiments, the changes may be substitution of an amino acid molecule, resulting in an addition of a glycosylation site, thereby increasing glycosylation of the polypeptide.

Typically, the present invention encompasses derivatives of the polypeptides/proteins. The term "derivative" or "chemical derivative" includes any chemical derivative of the polypeptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide/protein derivative can differ from the natural sequence of the peptide/protein described herein, by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide/protein derivatives and analogs according to the principles of the present invention can also include side chain bond modifications, including but not limited to —CH2-NH—, —CH2-S—, —CH2-S═0, OC—NH—, —CH2-O—, —CH2-CH2-, S═C—NH—, and —CH═CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH═CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The peptide/protein analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide/protein analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide/protein analogs, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide/protein is capable of displaying the function of the protein disclosed in the invention.

The Composition

According to some embodiments of the present invention, there is provided a composition comprising a plurality of particles, as described herein, wherein the plurality of particles is in a form of a powder (e.g., substantially dry powder, characterized by a water content less than 10%, less than 5%, less than 3%, less than 1% by weight of the composition). In some embodiments, at least a position of the plurality of particles within the powder is in a form of agglomerate of particles.

In some embodiments, the composition is a pharmaceutical or a nutraceutical, or a prebiotic composition, comprises a pharmaceutical or a nutraceutical or a prebiotic acceptable carrier, respectively. In some embodiments, the pharmaceutical or a nutraceutical or a prebiotic acceptable carrier is an aqueous solution. In some embodiments, the composition is in a form of an aqueous suspension, or dispersion. In some embodiments, the composition in the form of an emulsion.

In some embodiments, the pharmaceutical or a nutraceutical or a prebiotic composition, comprises an effective amount (such as a pharmaceutically or a nutraceutically effective amount) of the particles of the invention. In some embodiments, effective amount comprises at least 10%, at least 20%, at least 30%, at least 50%, at least 70%, at least 80% by weight of the particles, relative to the total weight of the pharmaceutical and/or of the nutraceutical and/or of the prebiotic composition.

In some embodiments, the composition is formulated for oral administration. In some embodiments, the oral composition is selected from, without being limited thereto, a tablet, a capsule, a syrup, a suspension, a beverage or a food product.

Oral administration, in one embodiment, comprises a unit dosage comprising a particle and/or a composition as described herein in a form comprising tablets, capsules, lozenges, chewable tablets, suspensions, emulsions and the like. Such unit dosage forms comprise a safe and effective amount of the desired therapeutic or nutraceutical or a prebiotic compound or compounds, each of which is in one embodiment, from about 0.1-20 g, or about 1-20 gram e.g., per daily use.

In some embodiments, tablets comprising particles and/or composition as described herein further comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc.

In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like comprising a particle and/or a composition comprising a particle as described herein. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, the composition is a pharmaceutical composition. In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

The compositions also comprise, in some embodiments, preservatives, such as sodium sorbate, benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed.

In another embodiment, the particle and/or the composition comprising the particle as described herein can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the particle and/or the composition comprising the particle as described herein is in powder form for constitution with a suitable vehicle, e.g., sterile, pyrogen-free water based solution, before use.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the particle and/or the composition comprising the particle as described herein are contained in an amount effective to achieve the intended purpose. In some embodiments, a therapeutically effective amount means an amount of the particle and/or the composition comprising the particle as described herein effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

The compositions also include incorporation of the particle and/or the composition comprising the particle as described herein into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In some embodiments, the particle and/or the composition comprising the particle as described herein is modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In one embodiment, the modifications also increase the compound's solubility in aqueous solution, eliminate aggregation, enhance the physical and chemical stability of the compound, and reduce the immunogenicity and reactivity of the compound. In another embodiment, the desired in vivo biological activity is achieved by the administration of such polymer-compound adducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity, and therapeutic efficacy of the particle and/or the composition comprising the particle as described herein described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a further compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more, unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Delivery Methods

According to some embodiments of the present invention, there is provided a method of delivering an agent to the gastrointestinal tract of a subject, comprising the step of administering to the subject a nutritionally or a therapeutically effective amount of the composition described herein. In some embodiments, the delivering is to a location selected from the intestine, the distal gut, or the colon of the subject. In some embodiments, the agent is a therapeutic agent. In some embodiments, the agent is a prebiotic nutritional agent. In some embodiments, the agent is a prebiotic growth factor.

In some embodiments, the prebiotic carbohydrate forming the corona of the particles of this invention have increased affinity or specificity or selectivity to transporters or other membrane proteins of a population of probiotic bacteria.

In some embodiments, the population of probiotic bacteria being targeted using the particles and compositions of the invention comprise at least one species selected from lactobacilli and bifidobacteria. Additional non-limiting examples of targeted probiotic bacteria include probiotic *enterococcus, lactococcus* and any other probiotic bacteria typically residing in the gastrointestinal tract of a human (or a pet or an animal such as of agricultural significance), and specifically the intestine, the distal gut and/or the colon.

In some embodiments, the carbohydrate described herein is resistant to degradation/absorption by the human gastrointestinal system. In some embodiments, the carbohydrate is selectively bound by a probiotic bacterium in a human intestine. In some embodiments, the carbohydrate is metabolized by a probiotic bacterium in a human intestine. In some embodiments, carbohydrate covalent linking to a protein prevents the absorption of the protein in the small intestine.

According to some embodiments of the present invention, there is provided a method of enriching probiotic bacteria in the intestine of a subject, comprising the step of administering to the subject the pharmaceutical and/or nutraceutical and/or a prebiotic composition described herein. In some embodiments, the method is for (i) increasing the abundance, and/or (ii) increasing activity of the probiotic bacteria in the intestine of a subject.

In some embodiments, increasing is by at least 2 times, 10 times, 100 times, 1000 times, 10.000 times, 100.000 times, 1000000 times or more, as compared to the same subject prior to administration of the pharmaceutical and/or nutraceutical and/or a prebiotic composition of the invention, including any range between.

In some embodiments, increasing activity comprises (i) increasing production, secretion, or both, of short chain fatty acids (SCFAs) such as, but not limited to, acetic, propionic, butyric, iso-butyric, iso-valeric etc.; (ii) reducing production, secretion, or both, of protein fermentation products such as ammonia, or phenol, cresol, or indole or branched chain fatty acids (BCFAs) (iii) any combination of (i) and (ii), by the probiotic bacteria. In some embodiments, increasing activity comprises (i) increased concentration of SCFA; and/or (ii) reduced concentration of protein fermentation products like ammonia within the colon of the subject supplemented with the pharmaceutical and/or nutraceutical and/or a prebiotic composition of the invention, as compared to the same subject before supplementation, or as compared to a similar subject which has not been supplemented with the pharmaceutical and/or nutraceutical and/or a prebiotic composition.

Short-chain fatty acid are well known in the art in include short chain alkyl (between 1 and 6 carbon atoms) carboxylic acids, such as butyric acid, acetic acid, propionic acid, etc., including any salt and any combination thereof. The SCFA/ammonia concentration within the colon of the subject can be determined according to the methods described herein.

In some embodiments, the probiotic bacteria (e.g., intestinal probiotic bacteria) belong to the genus *Akkermansia*. In some embodiments, the probiotic bacteria are or comprise *Akkermansia muciniphila*.

Techniques for formulation and administration of drugs are found in "Remington's Pharmaceutical Sciences," Mack Publishing Co., Easton, PA, latest edition, which is incorporated herein by reference.

In one embodiment, suitable routes of administration, for example, include oral, rectal, or intestinal delivery.

In some exemplary embodiments, the protein described herein is lactoferrin. In some embodiments, the lactoferrin further possesses anti-bacterial activity. In some embodiments, lactoferrin further possesses anti-viral activity. In some embodiments, lactoferrin further possessing an anti-fungal activity.

In some embodiments, the composition described herein is used for a targeted protein and/or growth factor delivery to a probiotic bacterium in a human intestine.

The Process

According to some embodiments of the present invention, there is provided a process for producing the particle described herein, the process comprises the steps of: (a) hydrolyzing a food grade protein by contacting the food grade protein with a protease in an aqueous solution under conditions suitable for hydrolysis thereof, thereby obtaining a plurality of peptides; (b) covalently bonding the plurality of peptides and a prebiotic carbohydrate(s) under conditions suitable for performing a Maillard reaction, thereby forming a plurality of Maillard conjugates; wherein:

the protease is selected from the group consisting of a gastric protease or an intestinal protease, including any functional derivative, or any combination thereof; the prebiotic carbohydrate is or comprises a mammalian milk oligosaccharide. In some embodiments, the prebiotic carbohydrate is or comprises FL.

In some embodiments, the method further comprises subjecting the plurality of Maillard conjugates to the conditions suitable for self-assembly of the Maillard conjugates, thereby forming the particles of the invention. In some embodiments, the method optionally comprises cross-linking at least a portion of the Maillard conjugates. In some embodiments, crosslinking is by reacting the Maillard conjugates with a crosslinking agent.

In some embodiments, the covalently bonding (e.g. conditions suitable for performing a Maillard reaction) comprises contacting the protein and the carbohydrate in an aqueous solution, and incubating the solution for 0.5-5 h at 40-100° C. In some embodiments, the covalently bonding comprises contacting the protein and the carbohydrate in an aqueous solution, drying the solution, thereby forming a powder; and incubating the powder at 50-70° C. at 75-85% relative humidity for 1-72 h.

In some embodiments, the crosslinking comprises providing the conjugate, adding a crosslinking compound at a pH solution of at least 8, and incubating the solution for 1-12 h at 20-50° C. In some embodiments, the crosslinking compound (or crosslinking agent) is selected from, without being limited thereto, sodium trimetaphosphate (STMP), monosodium phosphate (SOP), sodium tripolyphosphate (STPP), and phosphoryl chloride (POCL3), or any combination thereof. In some embodiments, the term "crosslinking compound" and the term "crosslinking agent" are used herein interchangeably.

In some embodiments, the crosslinking compound weight content, in solution of step (d), is in the range of 1% to 10%. In some embodiments, the crosslinker weight content is 1%, 2%, 3%, 4%, 5%, 6%, 7%, 8%, 9%, or 10%, including any value and range therebetween.

In some embodiments, step (b) is performed at a pH value range of 4 to 11, including any value and range therebetween. In some embodiments, step (b) is performed at a pH value range of 8 to 11, including any value and range therebetween. In some embodiments, step (b) is performed at a pH value of 4, 5, 6, 7, 8, 9, 10, or, 11, including any value and range therebetween. In some embodiments, step (b) is performed at a pH value of 8, 8.5, 9, 9.5, 10, 10.5, or 11, including any value and range therebetween. In some embodiments, step (b) is performed at a pH value of at least 10.

In some embodiments, step (a) comprises (i) contacting the protein with a protease in an aqueous solution, and (ii) incubating the solution for 0.5-5 h at 25-45° C. In some embodiments, the plurality of peptides is produced by an enzymatic hydrolysis or a chemical hydrolysis. In some embodiments, the gastric protease or an intestinal protease is selected from, without being limited thereto, pepsin, rennin, trypsin, and chymotrypsin, or any combination thereof. In some embodiments, step (a) is performed as described above, wherein the protease comprises a plurality of proteases. In some embodiments, step (a) is performed by subsequently hydrolyzing the protein with a first protease, and with a second protease. In some embodiments, step (a) is performed by simultaneously hydrolyzing the protein with a first protease, and with a second protease. In some embodiments, the first protease comprises pepsin. In some embodiments, the second protease comprises trypsin.

In some embodiments, the step a further comprises a step of activating the protease, comprising (a) incubating the solution of step (i) at pH 1-3, thereby activating the gastric enzyme, and (b) elevating pH to 6-8, thereby activating the intestinal enzyme.

In some embodiments, the process further comprises a step of entrapping an agent selected from, without being limited thereto, a prebiotic growth factor, a nutraceutical, a prebiotic nutritional agent, or a therapeutic agent, or any combination thereof, comprising: contacting the compound with the conjugate prior to step (c) described herein.

In some embodiments, the weight ratio of the protein to the carbohydrate in the solution of step (b) is in the range of 1:10 to 10:1, respectively, including any range between. In some embodiments, the weight ratio of the protein to the carbohydrate in the solution of step (b) is in the range of 1:5 to 5:1, respectively including any range between. In some embodiments, the weight ratio of the protein to the carbohydrate in the solution of step (b) is in the range of 1:2 to 2:1, respectively including any range between.

General

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" and "one" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Materials and Methods

Carbohydrate Analysis by High-Performance Anion Exchange Chromatography with Pulsed Amperometric Detection (HPAEC-PAD)

Monosaccharide and disaccharide quantification in the original and dialyzed GOS powders was carried out by high-performance anion-exchange chromatography with pulsed amperometric detection (HPAEC-PAD) (Dionex LC30, Sunnyvale, CA) with a pulsed amperometric detector (ED40) and a PA1 column. HPAEC-PAD was performed with eluent A (150 mM NaOH) and eluent B (150 mM NaOH and 500 mM sodium acetate). The elusion program: 0-1 min, isocratic elution using 100% A; 1-50 min, linear gradient to 0% A and 100% B. The elution rate was 1 ml/min. Analytical grade glucose and lactose were used as standards.

Conjugation Process by the Maillard Reaction

A solution of 83 mg/ml of lactoferrin and 630 U/ml of pepsin (Sigma) was prepared, and the pH was adjusted to 1.5, then it was stirred at 37° C. for 90 minutes. The pH was then raised to 10 with NaOH, and the solution was centrifuged at 4° C., 10,000 g to remove the insoluble peptides. The supernatant was filtered (0.45 μm, Thermo Scientific), resulting in LFH solution.

A solution of 250 mg/ml GOS was dialyzed in dialysis tubing with a MWCO of 500-1,000 Da (Spectrum Laboratories, Inc.) against DW for 24 hours. The retained solution was lyophilized, then reconstituted to obtain a 200 mg/ml aqueous solution, and the pH was raised to 10 with NaOH. The purity of the final GOS used was >95% (analyzed by HPAE-PAD).

The LFH solution was mixed into the GOS solution (final concentrations: 39.6 mg/ml LFH and 105.5 mg/ml GOS). The sample was stirred in a water bath at 70° C. for 50 minutes at a constantly adjusted pH=10. The pH was lowered to 7 with HCl to stop the reaction and the solution was dialyzed against distilled water in dialysis tubing with a MWCO of 2 kDa (Spectrum Laboratories, Inc.) to remove unconjugated GOS. The retained solution was lyophilized.

Estimation of the Extent of Conjugation by o-phthaldaldehyde (OPA) Assay

The extent of conjugation of GOS to LFH was estimated by the OPA assay. 100 ml of OPA reagent (Sigma) were prepared: 80 mg OPA were dissolved in 2 ml ethanol and added to 0.1 M sodium tetra borate pH 9.5 buffer. 5 ml of 20% SDS, 200 μl of 2-mercaptoethanol and 42.8 ml distilled water were added. 40 μl of sample were added to 1,600 μl OPA reagent and gently mixed. After 2 minutes the absorbance at 340 nm was recorded (Ultrospec 3000, GE Healthcare).

Sodium Dodecyl Sulfate Polyacrylamide Gel Electrophoresis (SDS-PAGE) Analysis

The Maillard conjugation progression, and later, the simulated digestion profiles of Maillard conjugates were performed via SDS-PAGE. 20% acrylamide gels were loaded with 50 μg digested protein samples, or 13 μg undigested protein samples. Electrophoresis was performed, gels were fixed, rinsed in DW and stained with Coomassie Brilliant Blue R-250, washed and destained before imaging.

Total Carbohydrate Quantitation by Phenol-Sulfuric Acid Method

The carbohydrate content in the LFH-GOS Maillard conjugates was estimated according to the phenol-sulfuric acid method in a microplate format described previously (Masuko et al., 2005). Briefly, a calibration curve of glucose was prepared with DW (0-0.15 mg/ml). 50 μl of sample were placed in wells of a 96-well microplate. 150 μl of concentrated sulfuric acid were added rapidly, and immediately 30 μl of a 5% phenol (w/v in DW) solution were added. The microplate was floated in a 90° C. water bath for 5 min. The plate was cooled and absorbance at 490 nm was measured (BioTek EON plate reader, Vermont, USA).

Protein Quantitation by the Lowry Method

The protein content in the LFH-GOS Maillard conjugates was estimated according to the Lowry method (Lowry, Rosebrough, Farr, & Randall, n.d.). 100 μl of 2 N NaOH were added to 100 μl of sample. The solution was hydrolyzed at 100° C. for 10 min. After cooling, 1 ml of complex-forming reagent (100:1:1 of 2% sodium carbonate, 1% copper(II) sulfate pentahydrate, 2% sodium potassium tartrate) was added. The solution remained at RT for 10 min. 100 μl of 1 N Folin-Ciocalteu's reagent was added and vortexed. The mixture remained at room temperature for 30-60 min and the absorbance was read at 750 nm (BioTek EON plate reader, Vermont, USA). Concentration was determined via a standard curve of 0-0.5 mg/ml bovine serum albumin (Sigma).

Conjugate Durability by Simulated Static In Vitro Digestion

The durability of the LFH-GOS Maillard conjugates to digestion was determined by simulated static in vitro digestion as previously described (Minekus et al., 2014). Briefly, in the gastric phase 1.2 ml of simulated gastric fluid (SGF) stock concentrated×1.25 were added to a sample of 1.5 ml LFH-GOS Maillard conjugates. The remaining 0.3 ml contained 200 μl of pepsin (P7000, Sigma) in 0.1 M HCl (final concentration 2000 U/ml) were added. The solution was adjusted to pH 3 with HCl and the volume was completed to 0.3 ml with water. The solution was stirred for 2 hours at 37° C. at a constant pH=3. In the intestinal phase, 2 ml of simulated intestinal fluid (SIF) stock concentrated×1.25 were added to 2.5 ml gastric digesta. The remaining 0.5 ml added, contained 1 M NaOH to raise the pH to 7, trypsin and chymotrypsin (trypsin: T0303; chymotrypsin: C4129, Sigma) at final concentrations of 100 and 25 U/ml, respectively, 134.4 μl of 100 mg/ml taurocholic acid sodium salt hydrate, 117.9 μl of 100 mg/ml sodium glycodeoxycholate, and water to complete the volume to 0.5 ml. The solution was stirred for 2 hours at 37° C. at a constant pH=7.

Particle Sizing by Dynamic Light Scattering (DLS)

Light scattering measurements were performed on a VASCO-2 particle size analyzer (Cordouan Technologies). 100 μl samples of conjugates in PBS (pH 2.8 and pH 6.7) were introduced into the cell at room temperature. Analysis of the data was performed using the nanoQ software (Cordouan Technologies).

Lactobacillus casei Growth Procedure for Conjugates Utilization Analysis

Modified MRS broth containing no carbon and no amino acid source (MRS-CP) was prepared. The broth contained 2 gr/L dipotassium hydrogen phosphate, 3 gr/L sodium acetate anhydrous, 2 gr/L triammonium citrate, 0.2 gr/L magnesium sulfate heptahydrate and 0.05 gr/L manganese sulfate tetrahydrate.

The MRS-CP broth was supplemented with 20 gr/L LFH-GOS conjugates powder (comprising 5 gr/L GOS and 15 gr/L LFH), that had undergone simulated static in vitro digestion, as previously described (in bacterial growth experiments, bile salts were not used as they inhibited bacterial growth, and in vivo are mostly re-absorbed in the intestine). A negative growth control was MRS-CP broth supplemented with water that had undergone the same simulated digestion process, instead of the LFH-GOS conjugates powder.

*L. casei* isolates were grown for 48 hours in commercial MRS broth. They were then inoculated in MRS-CP broth at an initial OD600 value of 0.1. Growth was monitored using a microplate spectrophotometer at 37° C. for 72 hours, reading absorbance at 600 nm. Experiments were performed in triplicate.

Evaluation of the Effect of Conjugation on *Lactobacillus casei* Growth

Modified MRS broth containing no carbon source (MRS-C) was prepared. The broth contained 4 gr/L yeast extract, 2 gr/L dipotassium hydrogen phosphate, 3 gr/L sodium acetate anhydrous, 2 gr/L triammonium citrate, 0.2 gr/L magnesium sulfate heptahydrate and 0.05 gr/L manganese sulfate tetrahydrate.

The MRS-C broth was supplemented with 20 gr/L LFH-GOS conjugates powder, or unconjugated LFH and GOS at the same amounts, that had undergone simulated static in vitro digestion, as described above. *L. casei* isolates were grown for 48 hours in commercial MRS broth. They were then inoculated in MRS-C broth at an initial OD600 value of 0.1. Growth was monitored using microplate spectrophotometer as described above.

Fabrication of 2'-FL-LFH

Briefly, LF was pre-hydrolyzed by digestive enzymes (pepsin and trypsin) and conjugated to 2'-FL using the Maillard reaction (pH 8.5, 80° C., 4 hr). Free 2'-FL was then removed from the solution using dialysis against DW. The unconjugated heated components were prepared by heating each component (2'-FL and LFH) separately, at the same conditions that were used for the Maillard reaction. Then, the heated components were mixed at an equivalent ratio to the conjugated components (20:80 2'-FL:LFH).

Animal Study

The effect of the 2'-FL-LFH conjugate and its compounds over the gut-microbiome was evaluated by a mice feeding experiment. 30 Female C57BL/6JRccHsd mice (8 weeks, —17 gr) were randomly sorted into 3 treatment groups (n=10). The first group was fed with 2'-FL-LFH, the second with unconjugated heated components of 2'-FL-LFH, and the third served as control and was treated with saline. Mice were orally gavaged 3 times a week, for 3 weeks, with 4.4 gr/kgBW of a treatment sample dissolved in 200 μl of DW. The gavage doses were chosen according to the estimated daily intake of 2'-FL in adults (5 gr per day, reported by the EFSA), with the addition of the conjugated protein (80%), while converting the doses from human to mouse.

Stool samples were collected on a weekly basis, starting from prior to the first gavage and during the three following weeks. Samples were collected into sterile tubes, kept on ice, and stored at −80° C. for further analysis of the gut-microbiome. After three weeks, all mice were sacrificed, and their colons were harvested. The content of each colon was gently extruded and collected, and immediately frozen and stored at −80° C. for further analysis of the metabolomic profile of gut-microbiota.

Animal trials were conducted at the Gutwirth Pre-Clinical Research Authority, Technion-Israel Institute of Technology. Mice were obtained from Envigo (Jerusalem, Israel) and housed in ventilated cages (20° C.-23° C., 12 light-hours a day). Mice received free access to autoclaved food and sterilized acidic water (pH=3.2±0.2) ad libitum. Experiments started following 2 weeks of adaptation. Animal studies were approved by the Technion—Israel Institute of Technology and the Israeli Ministry of Health (Pre-clinical research approval IL-035-03-2020). Mice exclusion criteria were loss of more than 20% of body weight, or improper gavage administration. Two mice were excluded from the unconjugated heated components control-group.

Determination of SCFAs in Colonic Contents

Briefly, the colonic samples (50 mg) were suspended in 125 μl of DW by vortexing for 20 min, and acidified with 8 μl of sulfuric acid (10%). Then, 200 μl of diethyl ether were added, and SCFAs were extracted by vortexing for 20 min. The mixture was centrifuged at 10,000 g for 10 min, and the diethyl ether fraction was analyzed using a 6890N GC instrument (Agilent Technologies, CA, USA), equipped with a capillary HP-5MS column (30 m×250 μm×0.25 μm, Agilent Technologies) coupled to a mass spectrometer. The temperature of the front inlet was set as 180° C., using a split mode (20:1). Helium was used as a carrier gas at a constant flow rate of 1 ml/min. The initial oven temperature was held at 50° C. for 5 min, ramped to 250° C. at a rate of 20° C./min, and finally held at this temperature for 1 min. The SCFAs were detected using a full scan mode. The MS source temperature was set to 230° C., and data were collected in the range of 30-400 atomic mass units (amu). The concentration of SCFAs was calculated using external standards, and expressed as μmol/gr sample. Data integration was performed with Agilent's MSD ChemStation.

Determination of Ammonia in Colonic Contents

The concentration of ammonia in colonic contents was analyzed using the phenol-hypochlorite method. Briefly, colonic samples (50 mg) were suspended in 500 μl of DW by vortexing for 20 min. The suspension was centrifuged at 10,000 g for 10 min, and the supernatant was collected. 0.5 ml of supernatant was mixed with 2.5 ml of freshly prepared phenol-reagent (5 gr phenol, 25 mg of sodium nitroprusside, and 500 ml of DW), and 2.5 ml of freshly prepared alkaline-hypochlorite-reagent (2.5 gr of sodium hydroxide, 26.85 gr of sodium phosphate dibasic dodecahydrate, 9.24 ml of sodium hypochlorite (11% of available chlorine), and 490 ml of DW). The mixture was incubated at 37° C. for 30 min to allow for color development. The absorbance at 625 nm was measured using a UV-visible spectrophotometer (Evolution 201, Thermo Scientific, Bargal, Shoham, Israel). The concentration of ammonia was calculated based on a calibration curve using ammonium sulfate as a standard.

Microbiota Composition Analysis

Total fecal DNA was extracted from stool samples using MagMAX™ CORE Nucleic Acid Purification Kit (ThermoFisher). The 16S rDNA was PCR-amplified using designated primers for the V3-V4 region (341F-806R). Samples were sequenced using the Illumina MiSeq platform (DNA Services Facility, University of Illinois Chicago, IL, USA). The Microbiome was profiled by QIIME2 (Ver. 2021.8). A minimum feature count of 23,241 was achieved. Taxonomy was assigned based on the Greengene database (13.8). Further LDA Effect Size (LEfSe) analysis was conducted using the Huttenhower lab Galaxy server. One mouse from the 2'-FL-LFH group and one from the unconjugated heated components control-group were removed due to low yield.

Statistical Analysis

The metabolic differences among groups in the in vivo study were analyzed using multiple student's t-tests. Statistically significant differences were accepted at $p<0.05$ level.

Example 1

Formation and Characteristics of an LFH-GOS Conjugate

As a non-limiting example, galacto-oligosaccharides (GOS) were selected as the model indigestible prebiotic carbohydrate, and lactoferrin was selected as the model protein. GOS are prebiotic carbohydrates synthesized from lactose, and are most commonly used in infant formulas. They are resistant to degradation in the human gastrointestinal tract by human digestive enzymes, but are metabolized by probiotic colon bacteria to lactate, short chain fatty acids (SCFAs), $CO_2$ and $H_2$. In a large number of human studies with consistent results, consumption of GOS led to selective stimulation of the health-beneficial bifidobacteria and lactobacilli- and supplementation of infant formula with GOS led to fecal abundance of those probiotics comparable to that of breast-fed infants (as human milk naturally contains large amounts of prebiotic oligosaccharides). In some in vitro studies, it was concluded that consumption of GOS may contribute to blocking the adherence of pathogens to the host gastrointestinal epithelial cells. GOS consumption may also enhance calcium absorption due to the reduction in pH caused by the formation of short chain fatty acids (SCFAs) in the colon, increasing calcium solubility and thus improving its absorption. GOS are considered GRAS (Generally Recognized as Safe) by the US FDA for various food categories, and in the European Union GOS can be used as a non-"Novel Food" ingredient in food products.

Lactoferrin (LF) is a natural protein found mostly in milk and whey. LF has been granted GRAS status by the US FDA and is added to commercial infant formula in some countries. Several of LF's known benefits include infection prevention, enhancement of early mucosal gut development and decrease of respiratory and gastrointestinal morbidity. LF also decreases gut colonization by parasites while promoting a bifidogenic microflora in the gut in neonates and preterm babies. In the stomach, pepsin digests LF to peptides. LF hydrolyzed by pepsin (LFH) was found to inhibit pathogens such as *Escherichia coli* and *Staphylococcus aureus* at concentrations of 16 and 8 mg/ml, respectively, while not inhibiting the growth of the beneficial lactobacilli and bifidobacteria under concentrations of ~64 mg/ml. LF peptides are *lactobacillus* and bifidobacteria growth factors, and therefore their use as part of the vehicle for delivery to the intestine could be beneficial, (and even synergistic with the oligosaccharides), to both the probiotic bacteria and to the human host.

By conjugating LFH to GOS the proteolysis (and consequently the absorption) of the LFH peptides in the small intestine is suppressed. Moreover, the conjugates can form self-assembled micellar particles whose outer surface is decorated by GOS, thus sterically inhibiting enzyme access, hence degradation of LFH peptides by gastrointestinal enzymes and digestive breakdown of any payload. This would increase the residual amounts of LFH and other vehicle's components reaching the intestine, to be selectively utilized by the probiotic bacteria there.

The formation of the LFH-GOS conjugates is shown in FIG. 1. The remaining free primary amino groups in the LFH, available for covalent conjugation to GOS units via the Maillard reaction, were quantified using the OPA assay. A reduction in free primary amino groups in the LFH is observed, until a plateau is reached after ~50 minutes of reaction time. This indicates that the primary amino groups had covalently bound to GOS via the Maillard reaction. Once the minimal value of free primary amino groups is reached, it is preferable to stop the reaction to prevent the formation of more advanced Maillard reaction products, including brown pigments (melanoidins). The progression of the Maillard conjugation was also monitored via SDS-PAGE (FIG. 1, right pane), in which the protein was stained with Coomassie Blue dye, and GOS remained unstained. This figure shows the molecular weight distribution of the conjugates during the progression of the Maillard reaction. Before the Maillard reaction commenced, the average molecular weight of the LFH was 5.2 kDa (bimodal distribution), and as the Maillard reaction progressed, an upwards smear formed, indicating an increase in molecular weight due to covalent bonding of GOS to the LFH peptides. The molecular weight distribution at the end of the reaction, and after lyophilization and reconstitution, ranged between ~2-20 kDa. As GOS are sugars of various degrees of polymerization, and LFH is also composed of polypeptides of various molecular weights, their addition products are bound to have various molecular weights too. Moreover, several GOS molecules may be bound to each peptide, resulting in a "smeared" band on SDS-PAGE. For the remaining experiments and analyses, the Maillard reaction was carried out at pH 10 and 70° C. for 50 minutes, the conjugates were isolated by dialysis, and the solution was lyophilized before further use. The goal was to characterize the conjugates and their performance in vitro.

The LFH-GOS conjugates powder component quantification, and particle size distribution in buffers of various pH values, is shown in Table 1.

TABLE 1

LFH-GOS Maillard conjugates powder characterization

| | | |
|---|---|---|
| Protein content % (W/W) | | 76 ± 1 |
| Carbohydrate content % (W/W) | | 25 ± 4 |
| Volume mean diameter ± standard deviation [nm] | pH 2.8 | 870 ± 380 |
| | pH 6.8 | 370 ± 130 |

The protein-to-carbohydrate ratio was about 3:1. This is presumably the highest amount of GOS that could be bound to the LFH under the aforementioned reaction conditions, as the GOS was in excess in the reaction solution. The pH values of the buffers selected for the particle size distribution analysis (Table 1), 2.8 and 6.8, represent pH values of various food products, such as acidic beverages and milk, respectively. Both samples exhibited multi-modal particle size distributions, with no particular trend in particle size with rising concentration between 0.1-20 mg/ml. This corresponds to the SDS-PAGE results in FIG. 1, in which a wide molecular weight distribution can be seen. As the molecular weights of the Maillard reaction products were highly varied, it expected that they would form self-assembled particles of various sizes. The relatively large particle sizes suggest that the self-assembled particles had formed aggregates. Based on the literature, the minimal particle size that can be detected by the palate is 25 μm. The particle size of the LFH-GOS conjugates in both buffers was under 2 μm so that they can therefore be added to food and beverages without harming smoothness.

Example 2

In Vitro Simulated Digestion Experiments

An in vitro simulated digestion experiment analyzed by SDS-PAGE (FIG. 2) showed that a significant portion of the protein in the Maillard conjugates survived both gastric and intestinal digestion, and is therefore expected to reach the colon in in vivo experiments as well, and be used by the colonic probiotic bacteria.

A solution of lactoferrin was hydrolyzed by pepsin at pH 2. A solution of galacto-oligosaccharides (GOS) was added to the lactoferrin hydrolysate (LFH) solution and the pH was raised to 10. The solution was heated, while stirring, for 50 minutes at 70° C. and to stop the Maillard reaction, the pH was lowered to 7 and the solution cooled down. The in vitro simulated digestion experiment was performed according to an international-consensus protocol with 2 hours of gastric digestion followed by 2 hours of small intestinal digestion. Materials surviving the entire intestinal phase are assumed to be capable of arriving at the colon. Following simulated digestion, the samples were analyzed by SDS-PAGE, where a band indicates a protein or a peptide, and the position of a band within each lane indicates its molecular weight.

Figure 2:
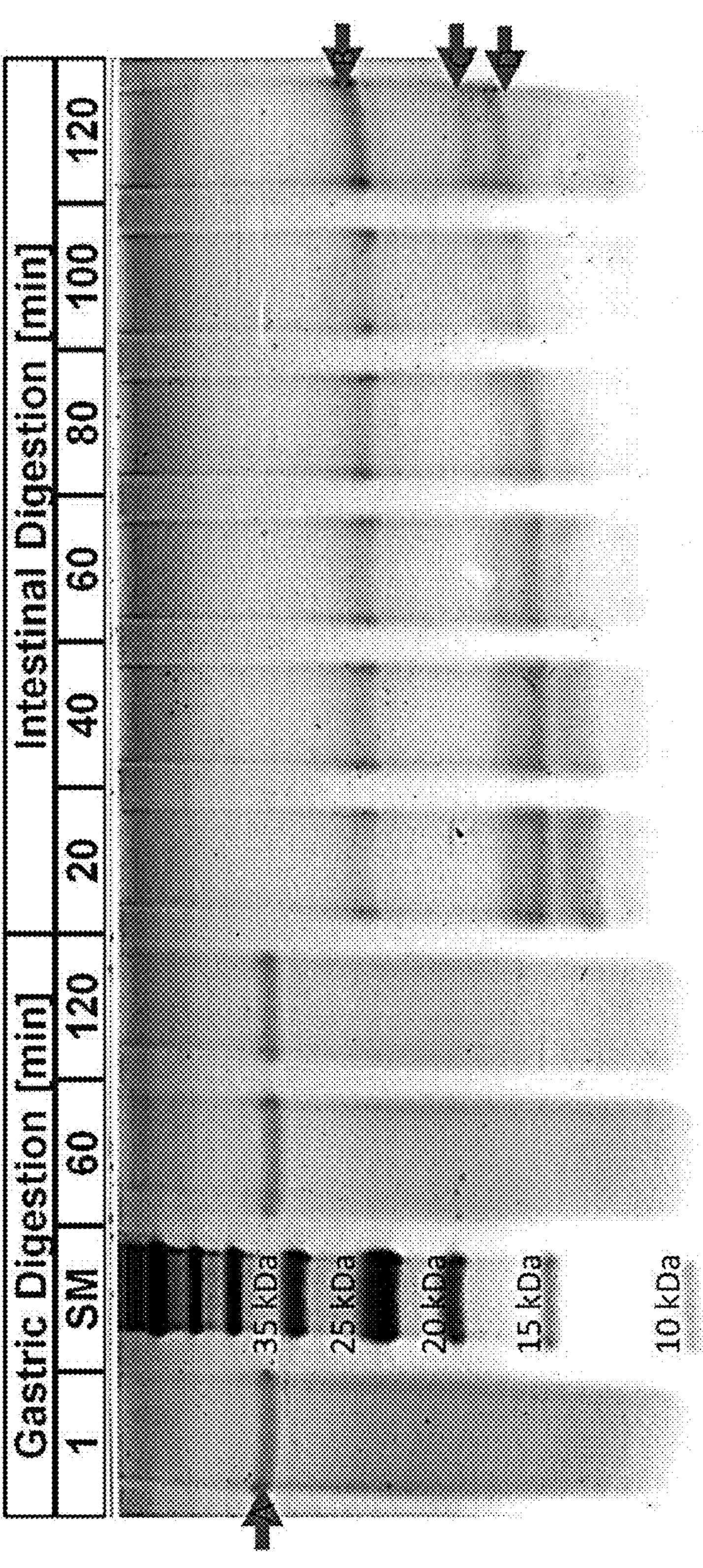
FIG. 2 presents the results of sodium dodecyl-sulphate gel electrophoresis (SDS-PAGE) following in vitro simulated adult-gastrointestinal-digestion of LFH-GOS conjugates. Arrows point to bands of the enzymes trypsin (B,C), chymotrypsin (D) and pepsin (A). SM=molecular weight size marker. The gray smeared band above 10 kDa, remaining almost unchanged during the entire digestion, indicates that most LFH-GOS particles endured gastrointestinal digestion.

FIG. 2 shows the SDS-PAGE analysis of LFH-GOS conjugates during in vitro simulated adult gastrointestinal digestion. Arrows point to bands of the enzymes trypsin (B,C), chymotrypsin (D) and pepsin (A). SM=molecular weight size marker.

Unprotected proteins are normally digested into small peptides and amino acids during the first minutes of adult intestinal digestion. In the case of the LFH-GOS conjugates, the lane at 1 minute of gastric digestion, which represents the beginning of the simulated digestion, shows a long smear—representing the undigested LFH-GOS conjugates with various molecular weights, ranging predominantly from 10 to 35 kDa but also higher. After 120 minutes of gastric digestion, the long smear seems largely unchanged, indicating that most LFH-GOS particles endured gastric digestion. This result was expected, as the lactoferrin was pre-digested with pepsin prior to conjugation with GOS, and the LFH-GOS particles were thus expected to be resistant to peptic digestion. During intestinal digestion, a slight modification of the LFH-GOS smear can be observed (disregarding the bands of the added enzymes), though by the end of 120 minutes of intestinal digestion a significant amount of smeared band can still be observed.

Conjugation of sugars to proteins via the Maillard reaction reduces the digestibility of the protein. The protein content of the LFH-GOS conjugates was protected from proteolysis during simulated gastrointestinal digestion thanks to pre-digestion with pepsin, and to the conjugation with the indigestible GOS, which also apparently led to conjugate self-assembly with the peptides at the core—hence protected by the corona of the oligosaccharides from further enzymatic digestion by trypsin and chymotrypsin. As a significant portion of the protein in the Maillard conjugates endured both gastric and intestinal digestion, it is expected to reach the colon in in vivo experiments as well, and be utilized by the colonic probiotic bacteria. In fact, the oligosaccharides, for which probiotic bacteria are believed to have specific transporters are expected to serve as an active targeting mechanism, analogously to selective active targeting to cancer cells, and to be selectively bound by these transporters, expressed uniquely by probiotic bacteria.

Example 3

In Vitro Utilization of LFH-GOS Conjugates by *L. casei*

*L. casei* was selected as a model probiotic bacterium to evaluate the ability of probiotic bacteria to utilize the LFH-GOS conjugates as a carbohydrate and amino acid source, and to establish the impact of the Maillard conjugation on the ability of probiotic bacteria to utilize LFH-GOS conjugates compared with the utilization of the unconjugated components.

Figure 3:
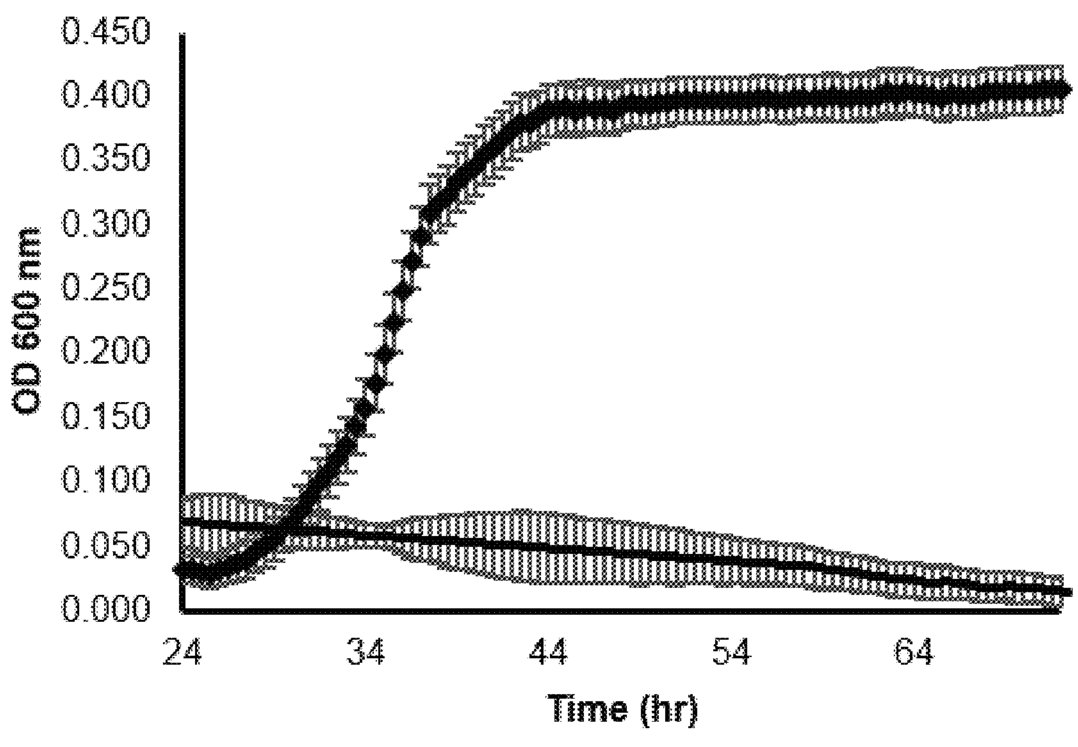
FIG. 3 presents the growth curve of *L. casei* on a minimal growth medium, plus LFH-GOS conjugates, which had undergone simulated digestion, as the sole carbohydrate and amino acid source (♦). The negative control (–) contained minimal growth medium plus water (in place of the LFH-GOS conjugates) that had undergone simulated digestion.

To simulate the process in the human body, the LFH-GOS conjugates underwent simulated gastrointestinal digestion prior to their addition to the growth medium. The growth curve of *L. casei* on a minimal growth medium containing the digested LFH-GOS conjugates as the sole carbohydrate and amino acid source is shown in FIG. 3.

To evaluate the effect of the Maillard conjugation on the ability of *L. casei* to utilize LFH and GOS as a carbohydrate and amino acid source, *L. casei* were grown on a minimal growth medium containing either LFH-GOS conjugates or unconjugated LFH and GOS at same concentrations as in the conjugate-containing medium. Both samples had undergone simulated gastrointestinal digestion. These growth curves are shown in FIG. 4.

Figure 4:
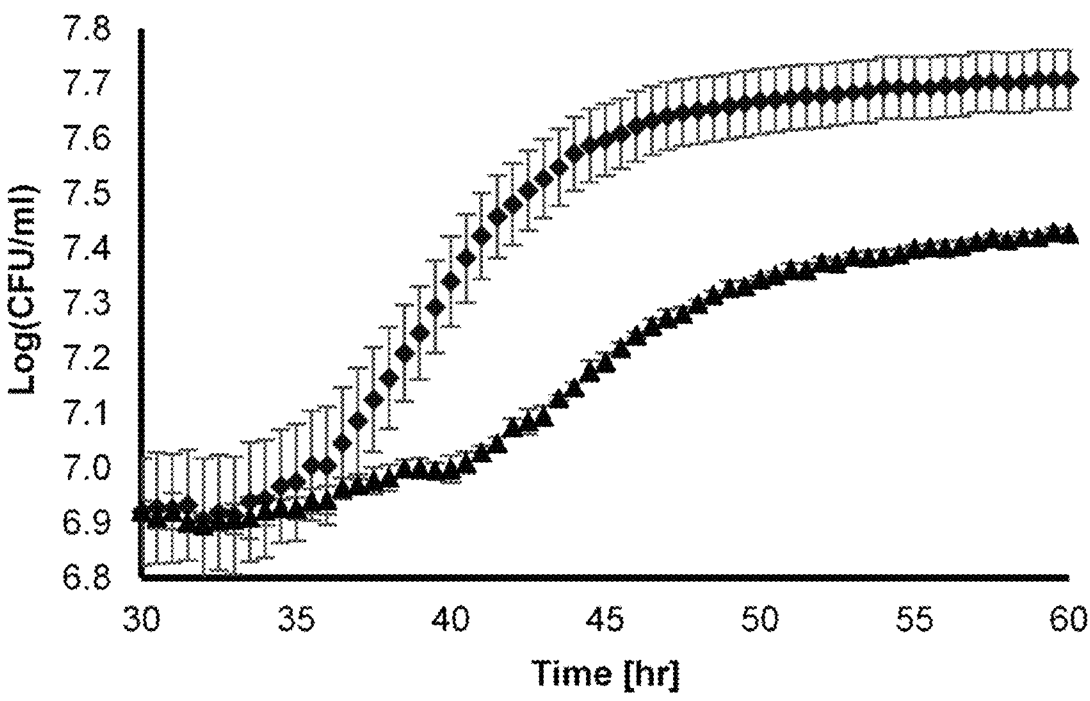
FIG. 4 presents a comparison of *L. casei* growth on a minimal growth medium containing either LFH-GOS conjugates (♦) or unconjugated LFH and GOS at same respective concentrations (▲) as sole carbohydrate and nitrogen source. Both samples underwent simulated gastrointestinal digestion prior to addition to growth media. The bacterial growth on the conjugates is superior to that on their unconjugated components (growth rates on LFH-GOS conjugates were 2-fold higher compared to the unconjugated components: 0.082 and 0.041 $hr^{-1}$, respectively).

FIG. 4 shows that the Maillard conjugation of GOS to LFH dramatically, and quite surprisingly, improved the ability of *L. casei* to utilize the components compared to unconjugated GOS and LFH (growth rates on LFH-GOS conjugates were 2-fold higher compared to the unconjugated components: 0.082 and 0.041 hr-1, respectively). Presumably, the advantage of the conjugates would be even more pronounced if digestion products are removed by absorption. As previously stated, the protein component of the conjugates was protected during simulated digestion. In the LFH-GOS conjugates sample, at the end of digestion, the protein fraction was mainly comprised of (conjugated) peptides, whereas the protein fraction in the unconjugated components sample underwent complete proteolysis and was comprised of mainly amino acids. Peptides are the preferred substrates for many colonic bacteria due to kinetic advantages of peptide-uptake systems in comparison with those for free amino acids, partially explaining the superior growth rate of *L. casei* on the conjugates. Without wishing to be bound to any mechanism of action, a possible explanation is that transporters on the cell surface of lactobacilli, which are involved in GOS uptake, had bound the GOS fraction and started its uptake. Although transporter specificity would not enable peptide uptake via an oligosaccharide transporter, still the consequent proximity of the GOS-conjugated protein fraction to the bacterium, would facilitate the utilization of the attached protein fraction, by excreted proteases and peptide transporters. Though much is still undiscovered about mechanisms of GOS utilization by probiotic bacteria, lactobacilli have been shown to utilize GOS in two major pathways: the first is transport and phosphorylation by the LacEF system and hydrolysis by the phospho-β-galactosidase LacG, and the second is by transport by LacS, the lactose permease, followed by hydrolysis by β-galactosidase. It is thus possible that conjugation of GOS to LFH allows selective binding of the LFH-GOS conjugates by probiotic bacteria capable of utilizing GOS, and consequently, these conjugates selectively support the growth and proliferation of these probiotics in the intestine, particularly the colon by selectively providing them with both carbohydrates and amino acids.

Example 4

A Crosslinked Carbohydrate Particle

Variations of the Maillard conjugates which have the potential to selectively benefit the probiotic bacteria in the intestine in vivo, and be economically attractive, are prepared. Conjugates of lactoferrin digested by pepsin (LFP) and galactooligosaccharides (GOS) with an average degree of polymerization (DP)~5 have been already developed. The conjugation of LFP to different indigestible prebiotic carbohydrates: FOS (DP~10) and inulin (DP~23) is assessed. In order to increase vehicle robustness, cross-linking of the carbohydrate fraction using sodium trimetaphosphate (STMP), an inexpensive food-grade cross-linker used in the starch industry, is examined. Crosslinking should protect the protein from protease accessibility, so that predigestion would not be necessary.

Example 5

Particle of the Invention Increases Concentration of SCFAs in Colonic Contents of Mice GC-MS SCFAs analysis of the extracted colonic contents of mice revealed that the most abundant SCFAs in all samples were acetic, propionic, and butyric acids. In FIGS. 5B-5E and 9, it is shown that the consumption of 2'-FL-LFH significantly increased the total SCFAs, acetic- and propionic-acid concentrations in the colonic contents of mice 1.1-1.3-fold compared with those of the unconjugated-components control-group, and 1.6-2.2-fold compared to the saline (blank) group. The concentration of butyric-acid was also significantly (1.7-fold) higher in the 2'-FL-LFH group vs. the blank-group. Additionally, the concentration of acetic, propionic, butyric, and total SCFAs in the unconjugated-components groups were significantly higher compared to the blank-group.

Ammonia in Mice Colon

Figures 5A, 5B, 5C:
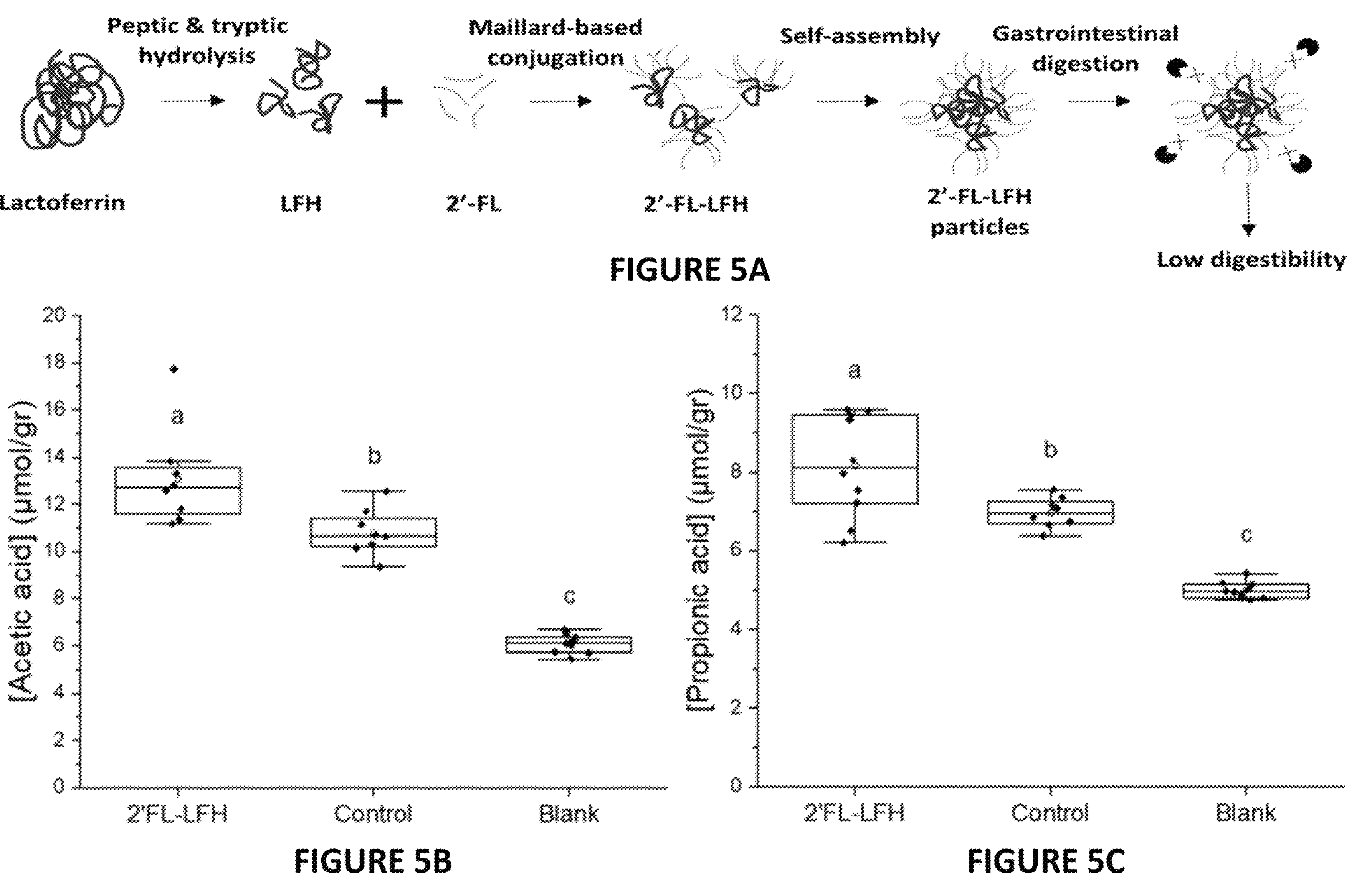
FIGS. 5A-5F include a scheme and box plots analysis of microbial metabolites. (5A) A non-limiting illustration of the formation process and structure of 2'-FL-LFH particles. Microbial metabolites concentration were quantified in mice colons of mice treated with supplementation of: 2'-FL-LFH; equidosed unconjugated, separately preheated components, representing the conventional prebiotic oligosaccharides approach (but normalized to include the same added protein; "Control"); and saline ("Blank"), following 3 weeks of dietary intervention. (5B) Acetic-acid; (5C) Propionic-acid, (5D) Butyric-acid, (5E) total SCFAs; and (5F) Ammonia concentration.
Figures 5D, 5E:
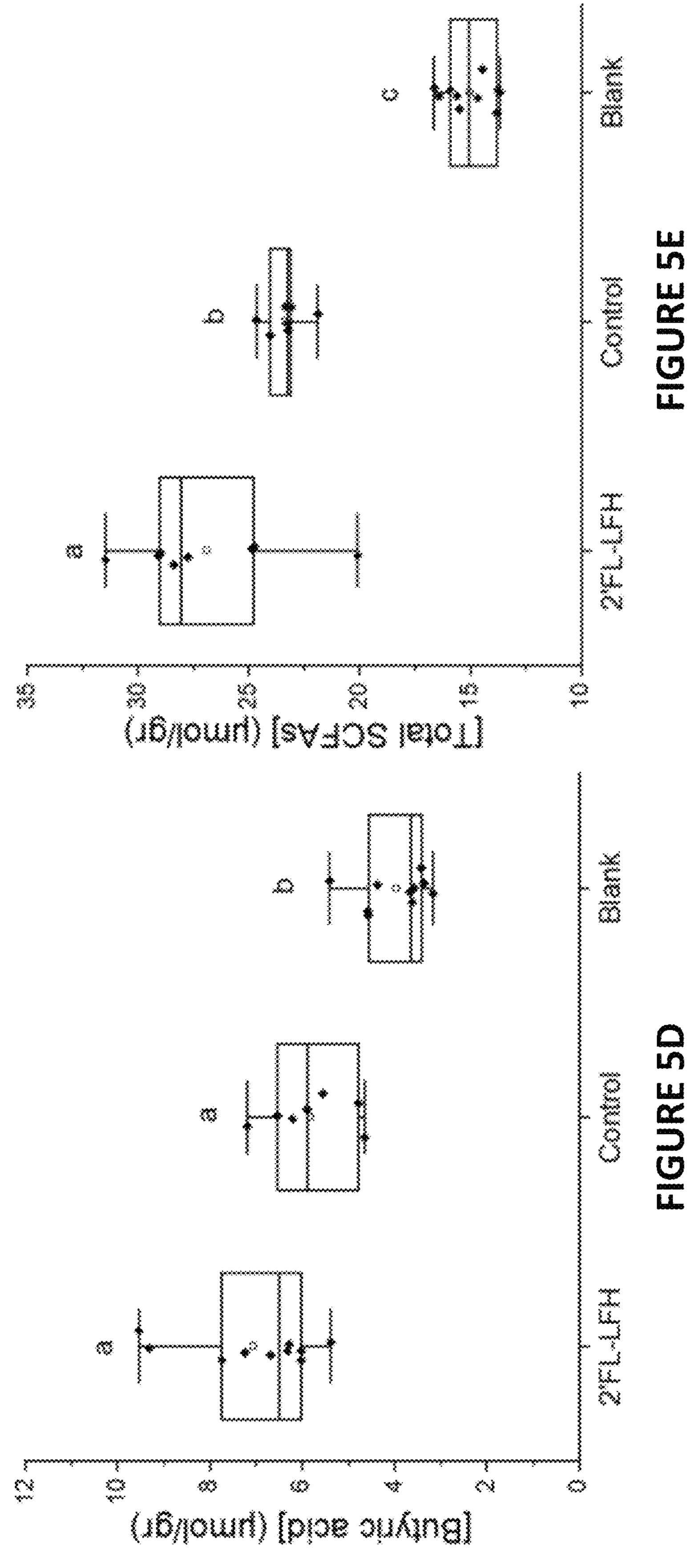
Figure 5F:
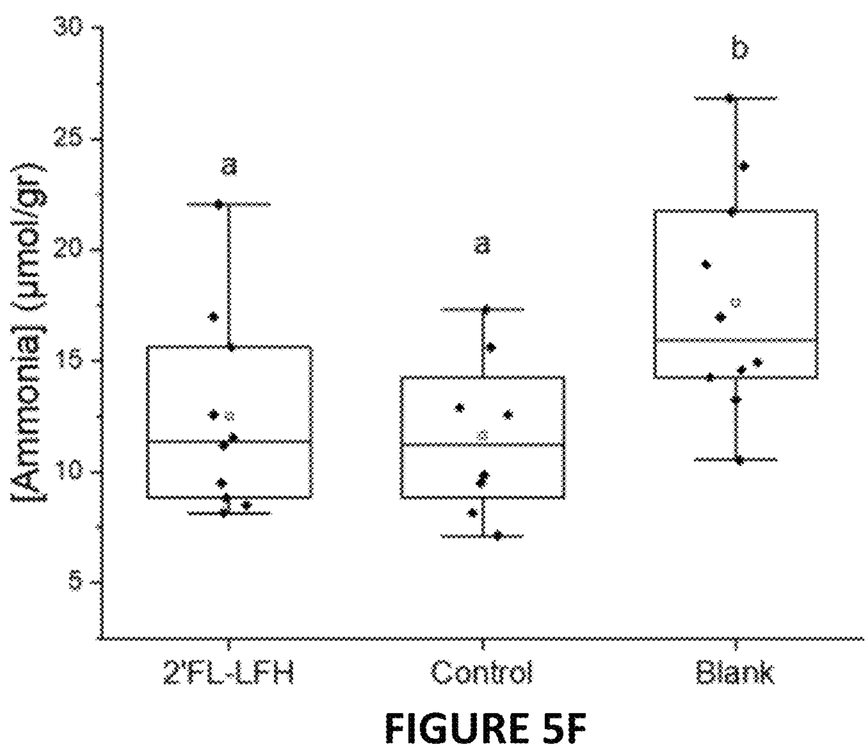
Figure 8:
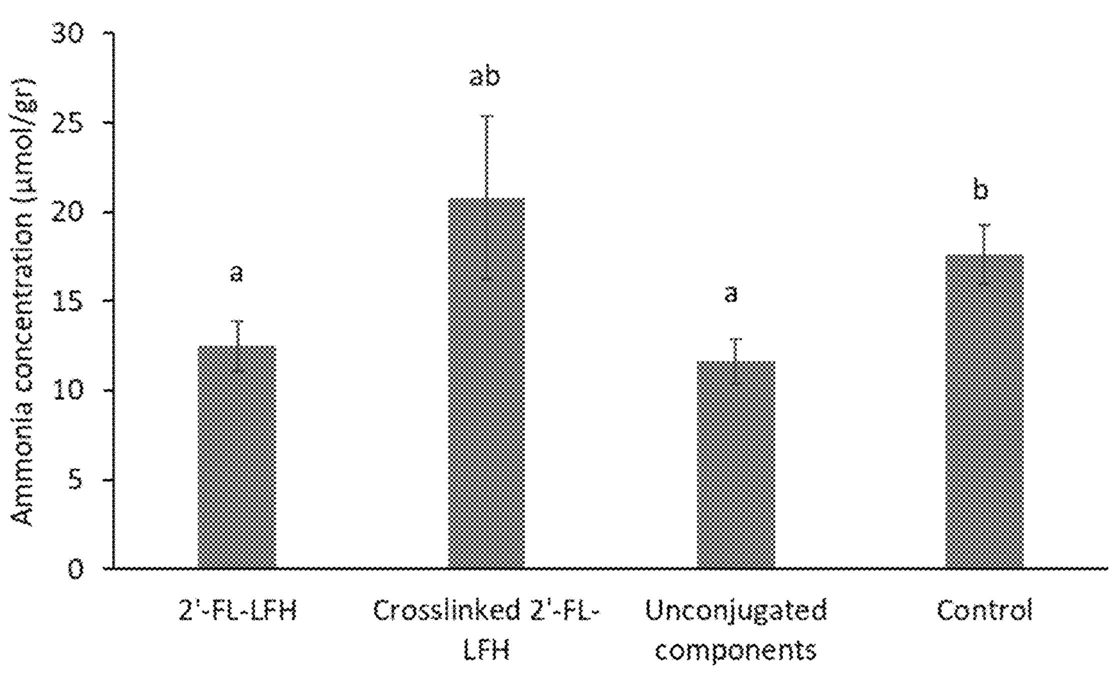
FIG. 8 includes a vertical bar graph showing ammonia concentration in colon content of mice of the different experimental groups.
Figure 9:
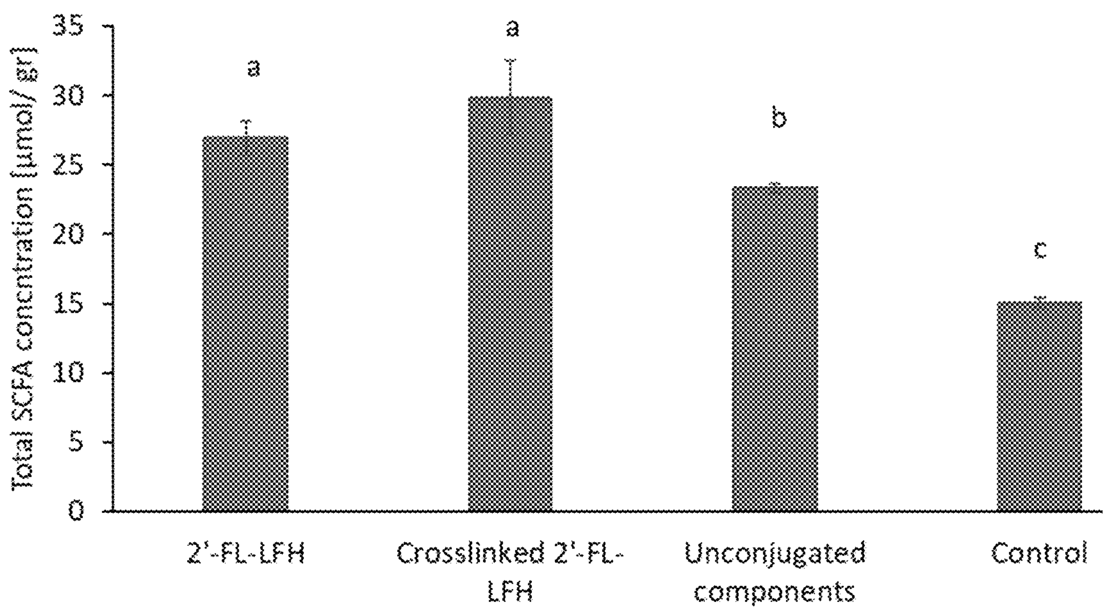
FIG. 9 includes a vertical bar graph showing total short-chain fatty acids (SCFAs) concentration in colon content of mice of the different experimental groups.

In FIGS. 5F and 8 it is shown that significantly lower levels of ammonia were determined in the colon of the 2'-FL-LFH group and the unconjugated-components control-group, compared to the blank and/or control group. The reduced ammonia production by gut-microbes can be associated with the abundance of fermentable-carbohydrates (2'-FL), as their microbial fermentation is more bio-energetically-favored compared to protein fermentation.

Example 6

Gut-Microbiome Composition

Figure 6A:
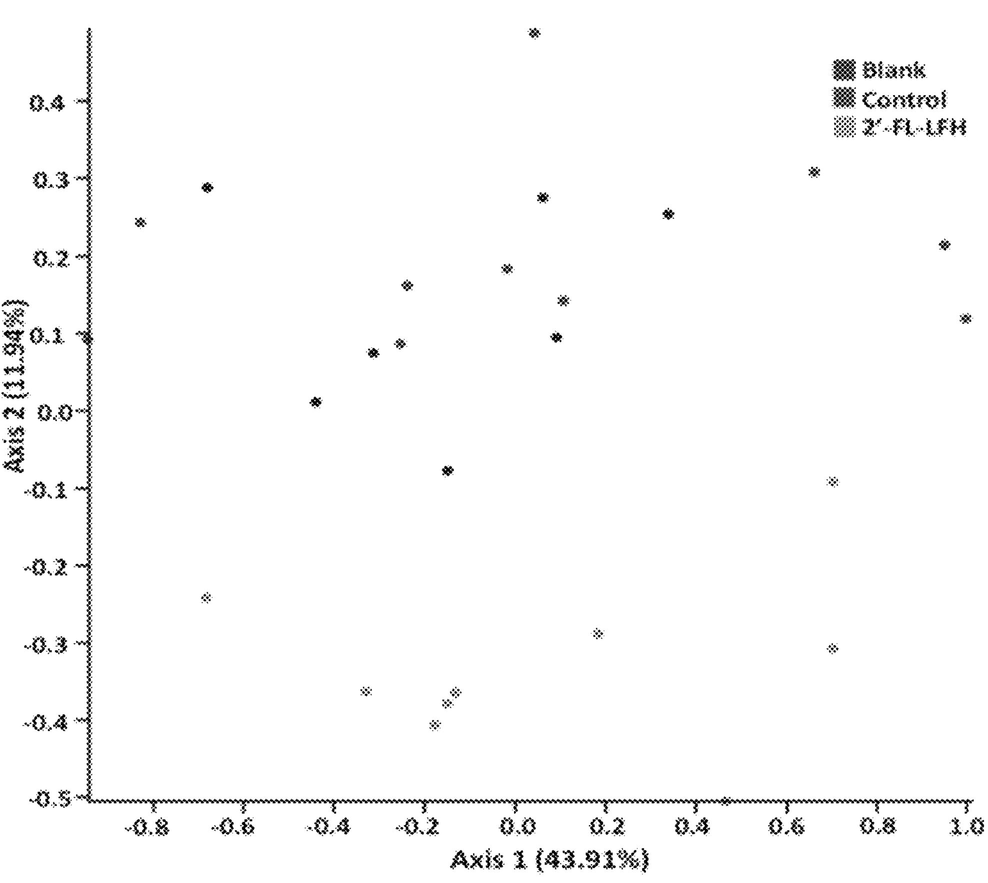

To assess the effect of 2'-FL-LFH on the gut-microbiome in the murine model, the gut-microbiome composition was profiled following a three-weeks feeding program, based on 16S rDNA stool-samples sequencing. FIG. 6A shows a weighted UniFrac (a phylogenetic-distance metric used for comparing biological communities) principal coordinate analysis (PCoA) of the gut-microbiome composition.

The microbiome profile of the 2'-FL-LFH group was distinct from the blank-group, along the second axis (11.94%). However, the PCoA plot depicts no significant changes in the microbial composition between the control (unconjugated, preheated-components) group and the blank (saline) group, along that axis.

Figure 7:
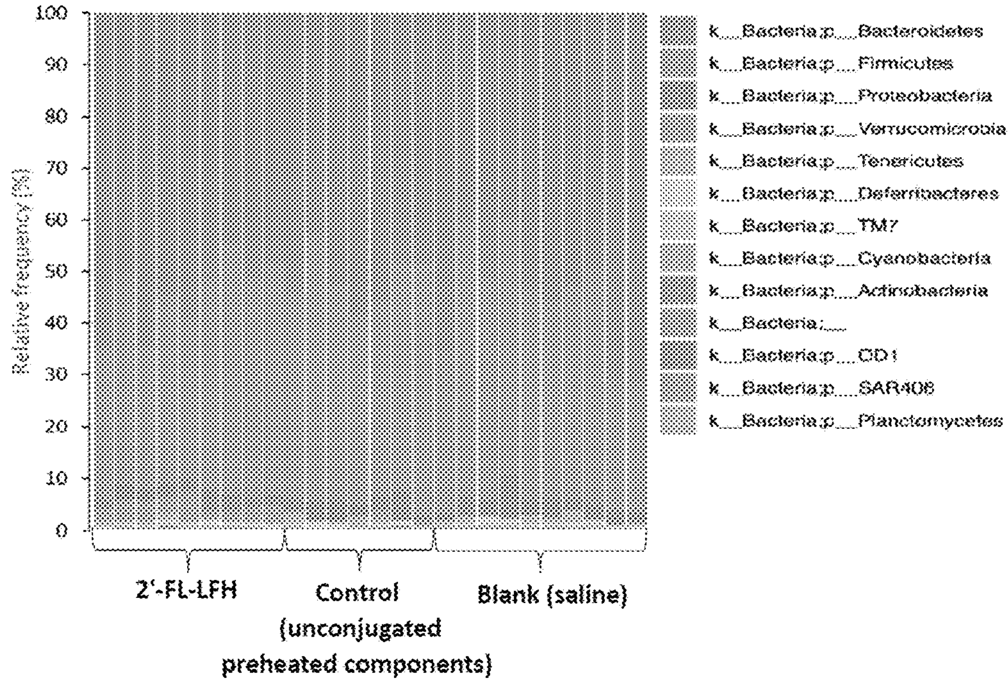
FIG. 7 includes a graph showing a microbial taxonomy profiling of the gut microbiome of each mouse following the relevant treatment. Taxonomy is ranked to the phylum level.

Taxonomy was assigned (based on the Greengene 16S-rRNA database ver. 18.3; FIG. 7), detailed to phylum-level, where mice across all treatments are relatively similar, except for *Verrucomicrobia* (pink), found to be more notable in the 2'-FL-LFH treated mice. This phylum was also found to be higher in the unconjugated control group, however, to a lesser extent compared to the 2'-FL-LFH group.

Figure 6B:
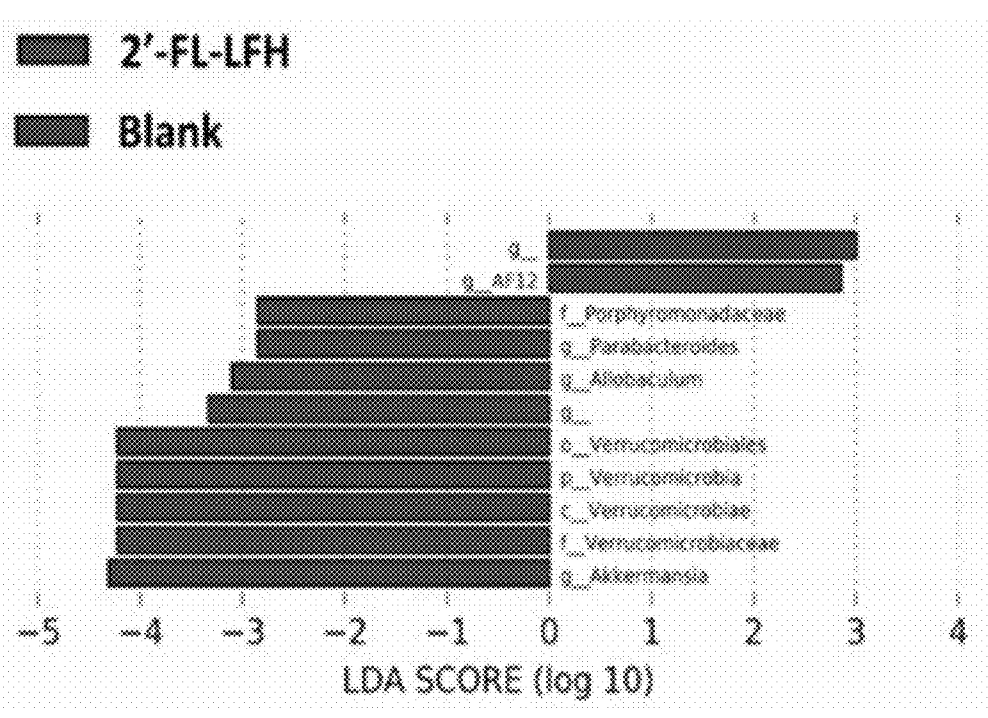
Figure 6C:
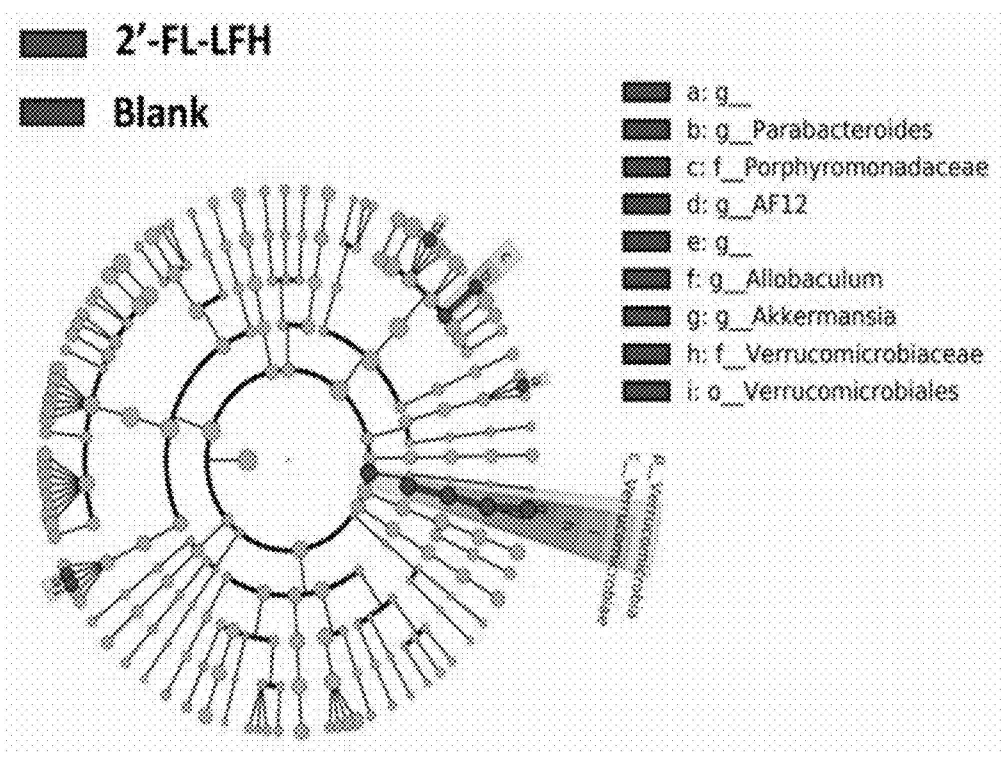

LEfSe (Linear discriminant analysis Effect Size) analysis was performed to identify the bacterial taxa most strongly correlated with differences between groups (FIGS. 6B-6E). The main bacterial genus shifted by the 2'-FL-LFH supplementation was the probiotic *Akkermansia* (FIG. 6B, LDA score=4.31, q-value=0.0002), belonging to the *Verrucomicrobia* phylum (FIG. 6C). This genus was also higher in the unconjugated control, compared to the blank-group, however, to a lesser extent (FIG. 6D LDA score=3.52, q-value=0.002). The Parabacteroides genus, previously found to increase following 2'-FL supplementation, was found to be higher in the 2'-FL-LFH group (FIG. 6B, LDA-score=2.85, q-value=0.003), compared to the blank. The consumption of 2'-FL-LFH also resulted in increased abundance of the *Allobaculum* genus, compared to the blank-group (FIG. 6B, LDA score=3.10, q-value=0.002). This shift was not observed in favor of the unconjugated control-group, compared to the blank-group (FIG. 6D).

Figure 6F:
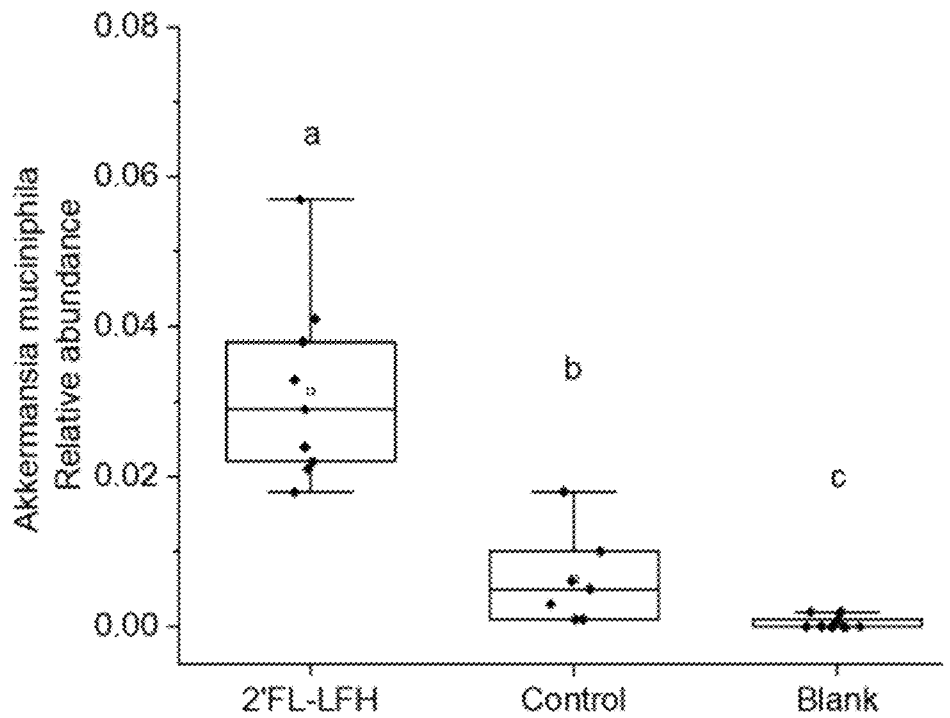
Figure 10:
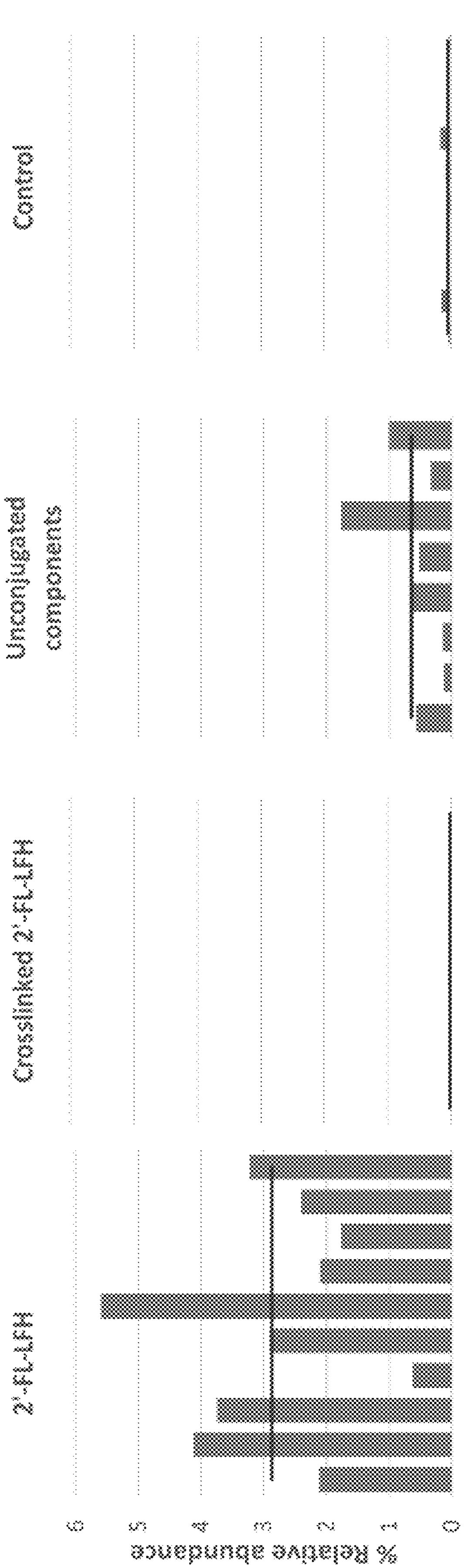
FIG. 10 includes a vertical bar graph showing the relative abundance of the *Akkermansia muciniphila* species in the different experimental groups.

As *Akkermansia* was the main bacterial genus found to significantly increase in the 2'-FL-LFH group, compared to the unconjugated control and the blank (FIGS. 6B, and 6D), the inventors further analyzed the relative abundance of the probiotic *A. muciniphila* species. Indeed, the relative abundance of *A. muciniphila* was found to be significantly higher in the 2'-FL-LFH group compared to the unconjugated control, while it was also significantly higher in the unconjugated control compared to the blank and/or control (FIGS. 6F and 10).

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A particle comprising a plurality of Maillard conjugates, wherein: each conjugate comprises a peptide covalently bound to a prebiotic carbohydrate; said peptide is a lactoferrin peptide obtained via hydrolysis of lactoferrin by a protease selected from the group consisting of: a gastric protease, an intestinal protease, or any combination thereof; and said prebiotic carbohydrate is 2'-Fucosyllactose.

2. The particle of claim 1, wherein said protease comprises at least two distinct protease species.

3. The particle of claim 1, wherein said plurality of Maillard conjugates are at least partially cross-linked within said particle.

4. The particle of claim 1, wherein said particle is a prebiotic particle.

5. The particle of claim 4, wherein administration of said prebiotic particle to a subject increases abundance of *Akkermansia muciniphila* in the colon of said subject.

6. The particle of claim 1, wherein (i) the average size of said particle is in the range of 10 nm to 3,000 nm; (ii) the weight ratio of said peptide to said prebiotic carbohydrate in said particle is in the range of 1:10 to 10:1, respectively; or (iii) any combination of (i) and (ii).

7. The particle of claim 1, wherein said particle comprises a core and a shell, wherein said core comprises at least 70% by weight of said peptide and said shell comprises at least 70% by weight of said prebiotic carbohydrate.

8. The particle of claim 7, wherein said core, said shell, or both further comprises a prebiotic nutritional agent, a therapeutic agent, a prebiotic growth factor, or any combination thereof.

9. A composition comprising a plurality of particles according to claim 1, wherein said composition is in a form of (i) a powder, or (ii) in a form of a suspension further comprising a nutraceutical or a pharmaceutically acceptable carrier; and wherein the particle is present within said composition in an amount effective to increase the abundance of *Akkermansia muciniphila* in the colon of a subject.

* * * * *